(12) United States Patent
Stamler et al.

(10) Patent No.: US 6,180,824 B1
(45) Date of Patent: Jan. 30, 2001

(54) MANIPULATING NITROSATIVE STRESS TO KILL PATHOLOGIC MICROBES, PATHOLOGIC HELMINTHS AND PATHOLOGICALLY, PROLIFERATING CELLS OR TO UPREGULATE NITROSATIVE STRESS DEFENSES

(75) Inventors: Jonathan S. Stamler, Chapel Hill, NC (US); Owen W. Griffith, Milwaukee, WI (US)

(73) Assignees: Duke University, Durham, NC (US); The Medical College of Wisconsin, Milwaukee, WI (US)

( * ) Notice: Under 35 U.S.C. 154(b), the term of this patent shall be extended for 0 days.

(21) Appl. No.: 09/361,167

(22) Filed: Jul. 27, 1999

Related U.S. Application Data

(62) Division of application No. 08/852,490, filed on May 7, 1997, now Pat. No. 6,057,367.
(60) Provisional application No. 60/025,819, filed on Aug. 30, 1996.

(51) Int. Cl.$^7$ .................................................. C07C 61/08
(52) U.S. Cl. ............................................................ 562/507
(58) Field of Search .................................... 514/562, 588, 514/863; 562/507

(56) References Cited

U.S. PATENT DOCUMENTS

| | | | |
|---|---|---|---|
| 3,968,249 | * 7/1976 | Bernstein et al. | 424/322 |
| 4,666,835 | 5/1987 | Baldwin et al. | 435/43 |
| 4,834,965 | 5/1989 | Martini et al. | 424/488 |
| 4,898,878 | 2/1990 | Shapiro et al. | 514/386 |
| 4,927,808 | 5/1990 | Kitahara et al. | 514/19 |
| 4,950,651 | 8/1990 | Suli et al. | 514/18 |
| 4,966,577 | 10/1990 | Crosson et al. | 664/20 |
| 5,112,954 | 5/1992 | Abrams et al. | 562/401 |
| 5,286,254 | 2/1994 | Shapland et al. | 604/21 |
| 5,290,571 | 3/1994 | Bounous et al. | 424/535 |
| 5,294,736 | 3/1994 | Griffith | 562/401 |
| 5,316,767 | 5/1994 | Hara et al. | 424/401 |
| 5,342,853 | 8/1994 | Mueller et al. | 514/523 |
| 5,362,309 | 11/1994 | Carter | 604/22 |
| 5,385,933 | * 1/1995 | Rabinovitz et al. | 514/499 |
| 5,385,937 | 1/1995 | Stamler et al. | 514/557 |
| 5,405,919 | 4/1995 | Keefer et al. | 525/377 |
| 5,427,797 | 6/1995 | Frostell et al. | 424/434 |
| 5,476,966 | 12/1995 | Anderson et al. | 562/507 |
| 5,525,357 | 6/1996 | Keefer et al. | 424/486 |
| 5,567,592 | 10/1996 | Benet et al. | 435/7.21 |
| 5,578,718 | 11/1996 | Cook et al. | 536/27.21 |
| 5,593,876 | 1/1997 | Stamler et al. | 435/188 |
| 5,616,775 | 4/1997 | Kronenthal | 560/9 |
| 5,628,730 | 5/1997 | Shapland et al. | 604/21 |
| 5,639,741 | 6/1997 | Witzel et al. | 514/80 |
| 5,641,754 | 6/1997 | Iversen | 514/44 |
| 6,011,067 | * 1/2000 | Hersh | 514/562 |

FOREIGN PATENT DOCUMENTS

WO9616645    6/1996 (WO).

OTHER PUBLICATIONS

Crooke, S. T., Hematologic Pathology, 9(2), 59–72 (1995).
Feelisch, M. and Stamler, J. S., Chapter 7 from Methods in Nitric Oxide Research, Feelisch and Stamler, eds., John Wiley & Sons, New York, 1996.
Griffith, O. W., et al, J. Biol. Chem. 254, 1205–1210 (1979).
Han, J., et al. in "The Biology of Nitric Oxide Part 5 Proceedings of the 4th International Meeting on The Biology of Nitric Oxide," Amelia Island, Florida, p. 114, Portland Press (Sep. 1995).
Hausladen, A., et al, Cell, vol. 86, 1–20 (Sep. 6, 1996).
Hirvonen, M–R, et al, Biochem. J. 315, 845–849 (1996).
Hamon, M., et al, Circulation, 90, 1357–1362 (1994).
DeGroote, M. A., et al, Science 272, 414–417 (Apr. 1996).
Pacelli, R., et al, Lancet, 347, 900 (1996).
Eskenazi, A. E., et al, J. Nat'l Cancer Instit., 85, 711–721.
Diaz Gomez, M. I., et al, Cancer Lett., 40, 257–263 (1988).
Alaoui–Jamali, M., et al, Cancer Chemo. Pharmacol., 34, 153–158 (1994).
Krauth–Siegel, R. L., et al, FASEB J., 9, 1138–1146 (1995).
Arrick, B. A., et al, J. Exp. Med. 153, 720–725 (1981).
Ramsay, et al., British Journal of Clinical Pathology 40, 101–102 (1995).
Mebmer, U. K., et al., FEBS Letters, 355, 23–26 (1994).
Andrew, P. J., et al., Biochem. Biophys. Res. Commun., 214, 949–946 (Sep. 25, 1995).
Held, K. D., et al., Mutation Research 299, 261–269 (1993).
Moore, W. K., et al., Proc. Natl. Acad. Sci. USA, 86, 1461–1464 (Mar. 1989).
Guillemard, E., et al., Antimicrobial Agents and Chemotherapy, 1057–1059 (Apr. 1996).

(List continued on next page.)

Primary Examiner—Kevin E. Weddington

(57) ABSTRACT

Mammals are treated for infection or for conditions associated with pathologically proliferating mammalian cell growth (for example, certain cancers, restenosis, benign prostatic hypertrophy) by administration of a manipulator of nitrosative stress to selectively kill or reduce the growth of the microbes or helminths causing the infection or of host cells infected with the microbes or of the pathologically proliferating mammalian cells. Novel agents include α-alkyl-S-alkyl-homocysteine sulfoximines wherein the α-alkyl contains 2 to 8 carbon atoms, and the S-alkyl-contains 1 to 10 carbon atoms. In another invention herein, mammals in need of increased nitrosative stress defenses are treated, e.g., humans at risk for a stroke because of having had a transient ischemic attack, are treated. Treatments to increase nitrosative stress defenses include, for example, repeated administrations of low doses of manipulators of nitrosative stress so that the subject treated has increased tolerance to nitrosative stress. In still another invention, mammals are treated for protozoal infections by systemic administration of L-buthionine-S-sulfoximine and agent that increases nitrosative stress.

15 Claims, 2 Drawing Sheets

OTHER PUBLICATIONS

Radomski, M. W., et al., Br. J. Pharmacol., 107, 745–749 (1992).
deBelder, A., et al., The Lancet, 345, 124–125 (Jan. 1995).
Young, D. B., et al., Annual Review of Microbiology, 49, 641–673 (1995).
Singh, R. J., et al., J. Biol. Chem., 271, 18596–18603 (Aug. 1996).
Struck, A. J., et al., FEBS Letters, 361, 291–294 (1995).
Wang, T., et al., Celluar Pharmacology, vol. 2, 237–240 (1995).
Yi–zun, J., et al., Chinese Medical Journal, 105, 647–654 (1992).
Wink, D. A., et al., J. Biol. Chem. 272, 11147–11151 (Apr. 1997).
Hausladen, A., et al., Cell, 86, 719–726 (Sep. 6, 1996).
Nathan, Carl F., et al., Immunology, 3, 65–70 (1991).

* cited by examiner

MANIPULATING NITROSATIVE STRESS TO KILL PATHOLOGIC MICROBES, PATHOLOGIC HELMINTHS AND PATHOLOGICALLY, PROLIFERATING CELLS OR TO UPREGULATE NITROSATIVE STRESS DEFENSES

CROSS-REFERENCE TO RELATED APPLICATION

This is a divisional of U.S. application Ser. No. 08/852,490, filed on May 7, 1997 now U.S. Pat. No. 6,037,367 which claims the benefit of U.S. Provisional Application No. 60/025,819, filed Aug. 30, 1996.

This invention was made at least in part with Government support under National Institutes of Health Grant Nos. DK48423, HL02582 and HL52529. The Government has certain rights in the invention.

TECHNICAL FIELD

One invention herein is directed to treating patients having pathological conditions involving proliferation of pathologic microbes or pathologic helminths or pathologically proliferating mammalian cells. Another invention herein is directed to treating patients in need of increased nitrosative stress defenses.

BACKGROUND OF THE INVENTION

Nitric oxide (NO) is now recognized as a signaling molecule in biology and has been implicated in the function of virtually every organ system in mammals. It is known that NO relaxes blood vessels, intestines, airways and skeletal muscles and plays a role in memory, sexual behavior and host defense. On the other hand, excessive production of NO has been implicated in organ dysfunction, degenerative disease and promotion of cancer. Arthritis, ulcerative colitis, Alzheimer's disease, congestive heart failure, septic shock and atherosclerosis are disorders in which NO may play a pathogenic role.

It is recognized that there is normally a certain amount of endogenously produced oxidative stress in mammals, i.e., the endogenous production of reactive oxygen species in the body, e.g., superoxide, hydrogen peroxide, hydroxyl radical, hypochlorous acid and singlet oxygen. This is thought to contribute to ageing, rheumatism, atherosclerosis, inflammation, respiratory distress syndrome, fibrosis, and development of infectious diseases such as AIDS.

Before the discovery leading to the inventions herein, it was not recognized that there is a nitrosative stress distinct from oxidative stress that affects mammals and also microorganisms which can be manipulated in a therapeutically effective manner, either by decreasing microbial, helminth or pathologically proliferating mammalian cell defenses against nitrosative stress or by imposing a nitrosative stress or by upregulating nitrosative stress defenses.

SUMMARY OF THE INVENTION

We turn firstly to the inventions herein related to manipulating nitrosative stress to kill or reduce the growth of pathologic microbes or pathologic helminths or pathologically proliferating mammalian cells.

It has been discovered that cells producing or exposed to nitric oxide related compounds as defined below are subjected to nitrosative stress.

The term "nitric oxide related compounds" is used herein to mean compounds able to transfer $NO^+$, $NO^-$ or $NO_2^+$ group to biological molecules. The term does not include nitric oxide itself. Nitric oxide itself is not a nitrosative stress agent.

The term "nitrosative stress" is used herein to mean an impetus for NO or $NO_2$ group attachment to proteins, nucleic acids or other biological molecules. It may be potentially therapeutic if microbes, helminths or pathologically proliferating mammalian cells are affected or potentially pathologic if normal mammalian cells are damaged. Nitrosative stress is distinct from oxidative stress and can occur under anaerobic conditions.

It has further been discovered that to prevent damage from nitrosative stress, cells exhibit constitutive defenses as well as an adaptive response that applies to microorganisms including bacteria as well as to helminths and to mammalian cells including human cells. An important aspect of this adaptive response is that it is distinct in its regulation and in its molecular purpose from the adaptive response to oxidative stress. Specifically, it has been discovered that cells upregulate resistance genes and other biochemical pathways to protect themselves from nitrosative stress. Thiols (e.g., glutathione in mammals and glutathione-producing helminths and microorganisms, L-homocysteine, mycothiol, ovothiols, etc.) and enzymes which mediate constitutive thiol synthesis comprise the first line of defense. Antinitrosative stress genes and their products comprise a second line of defense.

The term "antinitrosative stress gene" is used herein to mean a gene coding for a product that when expressed either breaks down or eliminates nitrosants (nitrosating species), denitrosates nitrosatively inhibited proteins or other biological molecules to restore their function, or upregulates other products or pathways which are protective against nitrosative stress.

An embodiment of the invention herein involves selective manipulation of nitrosative stress so that it selectively affects pathologic microbe proliferation or survival or pathologic helminth proliferation or survival or pathologic cell proliferation, growth or survival in mammals (including humans). This manipulation of nitrosative stress can be in microbes infecting the mammals or in mammalian cells infected with pathologic microbes to selectively kill or inhibit the microbes or the host cells containing the microbes or in pathologic helminths infecting the mammal to selectively kill or inhibit the helminths or in pathologically proliferating mammalian cells, e.g., to selectively kill target cells (e.g., proliferating cancer cells or cells proliferating to cause restenosis or benign prostatic hypertrophy). The invention of this embodiment is a method of inhibiting growth of pathologic microbes or pathologic helminths or pathologically proliferating mammalian cells, in a mammal, and comprises administering to said mammal a therapeutic pathologic microbe or pathologic helminth or pathologically proliferating mammalian cell antiproliferative effective amount of one or more manipulators of nitrosative stress in said microbes or in mammalian host cells infected with said microbes or in said helminths or in said pathologically proliferating cells whereby nitrosative stress selectively kills or reduces the growth of said microbes or helminths or mammalian cells or selectively enhances their susceptibility to innate immune defenses or the susceptibility of said microbes to antimicrobial agents (that function by a mechanism other than by manipulating nitrosative stress) or the susceptibility of said helminths to anthelmintic agents (which function by a mechanism other than by manipulating nitrosative stress) or the susceptibility of said pathologically proliferating mammalian cells to antiproliferation agents (that function by a mechanism other than by manipulating nitrosative stress); provided that when the pathologically proliferating mammalian cells are those that would cause restenosis, the manipulator(s) of nitrosative stress comprise (s) an inhibitor of protection against nitrosative stress and is (are) employed to selectively kill or reduce the growth of said cells or to enhance their susceptibility to antiproliferation agents, i.e., to anti-restenosis drugs that function by a mechanism other than by manipulating nitrosative stress.

The terms "pathologic microbes" and "pathologic microorganisms" as used herein mean pathologic microorganisms including but not limited to pathologic bacteria, pathologic viruses, pathologic Chlamydia, pathologic protozoa, pathologic Rickettsia, pathologic fungi, and pathologic mycoplasmata.

The term "host cells infected with pathologic microbes" includes not only mammalian cells infected with pathologic viruses but also mammalian cells containing intracellular bacteria or protozoa, e.g., macrophages containing *Mycobacterium tuberculosis, Mycobacterium leper* (leprosy), or *Salmonella typhi* (typhoid fever).

The term "pathologic helminths" as used herein refers to pathologic nematodes, pathologic trematodes and pathologic cestodes.

The term "pathologically proliferating mammalian cells" as used herein means cells of the mammal that grow in size or number in said mammal so as to cause a deleterious effect in the mammal or its organs.

The term "selectively kills or reduces the growth of said microbes or helminths or mammalian cells" as used herein means kills or reduces growth of pathologic microbes or host cells containing pathologic microbes or pathologic helminths or pathologically proliferating mammalian cells without causing unacceptable killing or inhibition of growth of normal mammalian cells or kills or reduces growth of mammalian host cells containing pathologic microbes or pathologically proliferating mammalian cells in a percentage which is at least 10% greater than the percentage of normal mammalian cells adversely affected.

The term "therapeutic pathologic microbe or pathologic helminth or pathologically proliferating mammalian cell antiproliferative effective amount" as used herein means amount causing reduction in rate of proliferation of at least 10%.

The term "antiproliferative agent" is used herein to mean anticancer agent useful to inhibit growth of pathologically proliferating cancer cells or anti-restenosis drug useful to inhibit growth of pathologically proliferating cells that would cause restenosis or drug used to inhibit growth of pathologically proliferating cells causing benign prostatic hypertrophy or drug inhibiting growth of other kinds of pathologically proliferating cells, that does not function by manipulating nitrosative stress.

So far as microbes are concerned, the method is for inhibiting growth of pathologic microbes in a mammal and said method comprises administering to said mammal a therapeutic pathologic microbe antiproliferative effective amount of one or more manipulators of nitrosative stress in said microbes or in host cells infected with said microbes whereby nitrosative stress selectively kills or reduces the growth of said microbes or enhances their susceptibility to innate immune defenses or their susceptibility to antimicrobial agents. In a narrow embodiment herein where the microbes are protozoa, the manipulator of nitrosative stress administered is one that increases nitrosative stress in the pathologic microbes, or a manipulator of nitrosative stress administered is one that selectively inhibits protection against nitrosative stress in the pathologic protozoa but does not increase nitrosative stress in the pathologic protozoa and other manipulator of nitrosative stress is also administered which increases nitrosative stress in the pathologic protozoa, or a manipulator of nitrosative stress is administered which is a selective inhibitor of thiol synthesis by the protozoa. In a narrow embodiment herein where manipulator of nitrosative stress is administered which inhibits OxyR transcription or translation in microbes containing OxyR, manipulator of nitrosative stress is also administered which increases nitrosative stress in the pathologic microbes containing OxyR or which inhibits protection against nitrosative stress in said microbes in a way other than by inhibiting OxyR transcription or translation.

So far as helminths are concerned, the method is for inhibiting the growth of pathologic helminths in a mammal and said method comprises administering to said mammal a therapeutic pathologic helminth antiproliferative effective amount of a manipulator of nitrosative stress in said helminths whereby nitrosative stress selectively kills or reduces the growth of said helminths or enhances their susceptibility to innate immune defenses or their susceptibility to anthelmintic agents.

So far as pathologically proliferating mammalian cells are concerned, the method is for inhibiting the growth of pathologically proliferating mammalian cells in a mammal and comprises administering to said mammal a therapeutic pathologically proliferating mammalian cell antiproliferative effective amount of one or more manipulators of nitrosative stress in said cells whereby nitrosative stress selectively kills or reduces the growth of said cells or enhances their susceptibility to innate immune defenses or enhances their susceptibility to antiproliferation agents; except that when the pathologically proliferating mammalian cells are those that would cause restenosis, the manipulator(s) of nitrosative stress comprise(s) an inhibitor of protection against nitrosative stress (e.g., one or more inhibitors of protection against nitrosative stress are used as the only kind of manipulator of nitrosative stress or two kinds of manipulators of nitrosative stress are employed where one kind of manipulator of nitrosative stress is inhibitor of protection against nitrosative stress and the other kind of manipulator of nitrosative stress is agent which increases nitrosative stress) and is (are) employed to selectively kill or reduce the growth of said cells or to enhance their susceptibility to antiproliferation agents, i.e., to anti-restenosis drugs that function by a mechanism other than by manipulating nitrosative stress.

We turn now to special cases mentioned above.

It is known in the prior art to inhibit growth of protozoa by inhibiting thiol synthesis therein. In this regard, see Arrick, B. A., Griffith, O. W., and Cerami, A. J., Exp. Med. 153, 720–725 (1981). However, the mechanism for growth inhibition of protozoa of inhibiting protection against nitrosative stress has not heretofore been known, and administration of microbe selective thiol production inhibiting agents to mammals to inhibit growth of protozoa therein is not exemplified in the prior art. Moreover, it is not known in the prior art to inhibit growth of protozoa in mammals by therapeutic administration to increase nitrosative stress therein. Furthermore, it is not known in the prior art to combine increased nitrosative stress with thiol depletion or other strategies for decreasing defenses against nitrosative stress, for inhibiting growth of protozoa in mammals.

It is known in the prior art that OxyR protects bacteria from oxidative stress but the role of OxyR in providing protection against nitrosative stress has not heretofore been known. In this regard, see Papp-Szabo, B., et al., Infection and Immunity 62, 2662–2668 (1994). Moreover, it is not known in the prior art to administer inhibitor of OxyR transcription or translation to mammals to inhibit growth of bacteria therein, and it is not known in the prior art to inhibit growth of or to kill bacteria by therapeutically increasing nitrosative stress therein.

It is known in the prior art to insert NO releasing stents during angioplasty. However, it is not known in the prior art to administer manipulator of nitrosative stress which inhibits protection against nitrosative stress to selectively kill or reduce the growth of pathologically proliferating cells that would cause restenosis or to selectively enhance their susceptibility to antiproliferation agents that function by a mechanism other than by manipulating nitrosative stress. Moreover, it is not known in the prior art to concurrently administer manipulator of nitrosative stress which increases nitrosative stress and manipulator of nitrosative stress which inhibits protection against nitrosative stress in the pathologically proliferating cells that would cause restenosis.

We turn now to various kinds of manipulators of nitrosative stress.

One kind of manipulator of nitrosative stress is a selective inhibitor of protection against nitrosative stress in the pathologic microbes or in host cells infected with pathologic microbes or in the pathologic helminths or in the pathologically proliferating mammalian cells. The term "selective inhibitor" is used in the prior sentence to refer to agent which in use downregulates nitrosative stress defense mechanism in the pathologic microbes or in mammalian host cells infected with pathologic microbes or in pathologic helminths or in pathologically proliferating mammalian cells so as to effect or mediate the selective killing or growth reduction recited above.

One kind of selective inhibitor of protection against nitrosative stress is a selective inhibitor of thiol synthesis or selective depleter of thiol in the pathologic microbes or in mammalian host cells infected with pathologic microbes or in pathologic helminths or in pathologically proliferating mammalian cells. The term "selective inhibitor of thiol synthesis" as used herein refers to synthesis from amino acids or other precursors and means a selective inhibition of a distinct enzyme present in the pathologic microbes or in the pathologic helminths (i.e., a microbe-selective or helminth selective thiol synthesis inhibiting agent) or to selective application or action of an inhibitor of thiol synthesis which is itself not selective for inhibition of thiol synthesis in pathologically proliferating microbes or helminths or mammalian cells but which achieves selective result because of coaction with drug that has more specific application or action or by virtue of local delivery. The term "selective depleter of thiol" as used herein means agents which conjugate with thiols; agents transferring nitroso (—NO) or nitro (—$NO_2$) groups to thiols which, when administered systemically to the mammal, are selective for pathologic microbes infecting the mammal, host cells containing pathologic microbes, pathologic helminths infecting the mammal or pathologically proliferating mammalian cells; alkylating agents administered systemically to a mammal to inhibit growth of pathologic microbes in the mammal infected with the microbes or to inhibit growth of pathologic helminths in the mammal infected with the helminths; depleters of thiol that are administered locally;

and prodrugs for agents causing thiol depletion, which are activated in pathologic microbes or in pathologic microbe-infected cells or in pathologic helminths. The term "selective depleter of thiol" as used herein excludes the systemic administration of alkylating agents to mammals to inhibit growth of pathologically proliferating mammalian cells, the systemic administration of agents which cause thiol oxidation to disulfides and the systemic administration of thiol reductase (e.g., glutathione reductase also known as glutathione disulfide reductase) inhibitors, except when these agents or inhibitors are used with agents that increase nitrosative stress.

Another kind of selective inhibitor of protection against nitrosative stress is a selective inhibitor of transcription or translation of an antinitrosative stress gene (as defined above) or a selective inhibitor of an antinitrosative stress gene product. OxyR is a transcription factor in E. coli and Salmonella which has been discovered by us to be upregulated by nitrosative stress as described in Hausladen, A., et al., Cell, Vol. 86, pages 11–20 (1996). As indicated above, in a narrow embodiment herein where manipulator of nitrosative stress is administered which inhibits the transcription factor OxyR in microbes containing it, manipulator of nitrosative stress is also administered which inhibits protection against nitrosative stress in the microbes in a way other than by inhibiting OxyR transcription or translation or which increases nitrosative stress, e.g., two kinds of manipulators of nitrosative stress are administered and one kind inhibits OxyR transcription or translation and the other kind selectively inhibits thiol synthesis or depletes thiol in the microbe or increases nitrosative stress in the microbe.

Another kind of manipulator of nitrosative stress useful in the method described above is an agent that selectively increases nitrosative stress in the pathologic microbes or in the pathologic helminths or in the pathologically proliferating mammalian cells. The term "agent that increases nitrosative stress" refers to an agent that imposes nitrosative stress and includes nitrosating agent, that is agent that transfers $NO^+$, $NO^-$ or $NO_2^+$ group, or prodrug causing this effect, or an agent that activates or induces nitric oxide synthase or nitrogen oxide producing enzyme where nitrogen oxide is in part converted to nitric oxide related compounds. In one embodiment herein, the manipulator of nitrosative stress is not agent that activates or induces mammalian nitric oxide synthase or other nitrogen oxide producing enzyme and nitrosative stress is not imposed by conversion of nitrogen oxide to nitric oxide related compounds in the body.

In one aspect of the invention, the inhibition is carried out on pathologic microbes or pathologic helminths and the manipulator of nitrosative stress is one that selectively delivers nitrosating agent to the pathologic microbes or to host cells containing the pathologic microbes or to the pathologic helminths, i.e., agent that transfers $NO^+$, $NO^-$ or $NO_2^+$ group to the pathologic microbes or to the pathologic helminths. This type of manipulator of nitrosative stress can be an organic or inorganic nitrate or nitrite that selectively delivers nitrosating agent to the microbes or helminths. Such manipulator of nitrosative stress can be selected from the group consisting of substrates for nitrite reductase or nitrate reductase and nitrogen-oxide substrates for microbial sulfite metabolizing enzymes. Another example of manipulator of nitrosative stress that selectively delivers nitrosating agent to the pathologic microbes or to host cells containing them or to the pathologic helminths is antibiotic or drug that kills or reduces growth of said microbes (including antiviral compounds) or helminths, substituted to transfer $NO^+$, $NO^-$ or $NO_2^+$ group, to the microbes or helminths.

In another aspect of the invention herein two kinds of manipulators of nitrosative stress in said microbes or in mammalian host cells infected with said microbes or in said helminths, or in said pathologically proliferating mammalian cells are employed and one kind is a selective inhibitor of protection against nitrosative stress in said microbes or in said host cells or in said helminths or in said pathologically proliferating mammalian cells, and the other kind is a selective increaser of nitrosative stress in said microbes or host cells or helminths or pathologically proliferating mammalian cells, or prodrug therefor, and either the inhibition of protection against nitrosative stress or the increase of nitrosative stress or both are selectively effected in said microbes or host cells or helminths or mammalian cells.

In still another aspect of the invention, a single agent is employed as the manipulator of nitrosative stress, which both inhibits protection against nitrosative stress and also causes increase of nitrosative stress in the pathologic microbes or in mammalian host cells infected with said microbes, or in the pathologic helminths or in the pathologically proliferating mammalian cells.

Specific applications of general methods described above include selectively killing or reducing growth of pathologic microbes, e.g., bacteria, infecting a mammal, selectively killing or reducing growth of pathologic helminths in a mammal, selectively killing or reducing growth of pathologically proliferating cancer cells in a mammal, selectively inhibiting the cell proliferation or enlargement that would cause restenosis (e.g., by administering the manipulator fastened to a stent), and selectively inhibiting the cell proliferation or enlargement that would cause benign prostatic hypertrophy (e.g., by local administration of the manipulator).

We turn now to the application of selectively killing or reducing the growth of pathologically proliferating cancer cells in a mammal.

A preferred agent administered to mammals with pathologically proliferating cancer cells to kill or reduce growth of cancer cells in the mammal is a chemotherapeutic agent which transfers or which has been derivatized to transfer $NO^+$, $NO^-$ or $NO_2^+$ group to said cells. For example, where the cancer cells are of a type which may be treated by administration of an alkylating agent, the manipulator of nitrosative stress is an alkylating agent which transfers $NO^+$, $NO^-$ or $NO_2^+$ group to the cancer cells or which has been derivatized to transfer $NO^+$, $NO^-$ or $NO_2^+$ group to the cancer cells. For example, where the pathologically proliferating cancer cells are of a type which may be treated by administration of melphalan, the manipulator of nitrosative stress may be melphalan derivatized to transfer $NO^+$, $NO^-$ or $NO_2^+$ group to the cancer cells being treated. In an embodiment herein, the agent administered to mammals with pathologically proliferating cancer cells is not agent with polymer bound nitric oxide releasing $N_2O_2^-$ functional groups.

In a preferred method directed to the application of killing or reducing growth of pathologically proliferating cancer cells in a mammal, two kinds of manipulators of nitrosative stress are administered to the mammal affected with cancer, and one kind is an inhibitor of protection against nitrosative stress and the other kind is an agent that increases nitrosative stress and very preferably one or both of these two kinds of manipulators of nitrosative stress are selective for this(these) effect(s) in the cancer cells.

We turn now to the application of selectively inhibiting the cell proliferation that would cause restenosis. The method herein is preferably carried out by fastening one or a plurality of kinds of the manipulators of nitrosative stress to a stent inserted during angioplasty. This provides local application of the manipulator(s) of nitrosative stress to pathologically proliferating cells that would cause restenosis. In an embodiment of the invention herein, a single agent or a plurality of agents are attached to a stent to perform both the function of inhibiting glutathione synthesis in the pathologically proliferating cells and the function of increasing nitrosative stress in the pathologically proliferating cells. In one example of this method, inhibitor of thiol synthesis or depleter of thiol is attached to and administered from a stent as the sole manipulator of nitrosative stress and the insertion of the stent with inhibitor of thiol synthesis or depleter of thiol thereon is optionally followed by administration of intravascular beta-, gamma- or X-ray radiation. In a preferred method herein two kinds of manipulators of nitrosative stress are administered and both are associated with a porous polymer coated on a stent whereby the two kinds of manipulators of nitrosative stress leach out of the porous polymer and contact the pathologically proliferating cells and one kind of manipulator of nitrosative stress is L-buthionine-S-sulfoximine and the other kind of manipulator of nitrosative stress is an agent that increases nitrosative stress or NO-substituted L-buthionine-S-sulfoximine is administered by being associated with a porous polymer coated on a stent. In other alternatives, L-buthionine-S-sulfoximine is fastened to and administered from a stent and agent that increases nitrosative stress is administered systemically or agent that increases nitrosative stress is attached to and administered from a stent and L-buthionine-S-sulfoximine is administered systemically.

We turn now the application of selectively inhibiting the cell proliferation that would cause benign prostatic hypertrophy. Methods herein for this application comprise local injection into the prostate of an agent that inhibits glutathione synthesis or depletes glutathione or the implantation in the prostate of a pellet associated with said agent or the systemic administration of glutathione synthesis inhibiting or depleting agent with co-administration of drug which does not manipulate nitrosative stress that inhibits benign prostatic hypertrophy or the systemic administration of conventional drug for treatment of benign prostate hypertrophy which has been NO-substituted.

Another embodiment herein is directed to treating infections of the oral cavity in a mammal comprising topically administering to the site of the infection, an infection reducing effective amount of a manipulator of nitrosative stress in the infection-causing organism, especially an S-nitrosothiol.

Another embodiment herein is directed to treating infected skin lesions in a mammal comprising topically administering to the skin lesions an infection reducing effective amount of S-nitrosothiol applied as S-nitrosothiol or which can be formed in situ from and after administration to the lesions of a mixture comprising inorganic nitrite, pharmacologically acceptable acid and thiol.

Another embodiment herein is directed to treating protozoal infections in a mammal and comprises systemically administering to said mammal an infection reducing amount of L-buthionine-S-sulfoximine and agent that increases nitrosative stress.

In another embodiment, an agent which increases oxidative stress is administered to mammal infected with a pathologic microbe or a pathologic helminth or afflicted with pathologically proliferating mammalian cells, concurrently with the manipulator of nitrosative stress, and the combination of said agent and said manipulator selectively kills or reduces the growth of the pathologic microbes or of the pathologic helminths or enhances their susceptibility to innate immune defenses or the susceptibility of said microbes to antimicrobial agents (which function by a mechanism other than by increasing oxidative stress or by manipulating nitrosative stress) or the susceptibility of said helminths to anthelmintic agents (which function by a mechanism other than by increasing oxidative stress or by manipulating nitrosative stress) or selectively kills or reduces the growth of the pathologically proliferating mammalian cells or enhances their susceptibility to innate immune defenses or to antiproliferation agents (which function by a mechanism other than by increasing oxidative stress or by manipulating nitrosative stress).

Another embodiment herein is directed to a method for inhibiting growth of pathologic microbes in a mammal (including humans), comprising administering to said mammal a therapeutic pathologic microbe antiproliferative effective amount of a metal chelating agent and of an agent that increases nitrosative stress.

Another embodiment herein is directed to a method of inhibiting growth of pathologic microbes or pathologic helminths or pathologically proliferating mammalian cells in a mammal comprising administering to said mammal a therapeutic pathologic microbe or pathologic helminth or pathologically proliferating mammalian cell antiproliferative effective amount of agent that converts endogenously produced NO in the microbe, helminth and/or mammal to nitric oxide related compound or to $NO^+$ or $NO^-$, especially redox active metal catalysts, preferably with administration of agent that causes increased NO production in the microbe, helminth and/or mammal, e.g., a cytokine to increase NO production in the mammal.

Another embodiment herein is directed to a method of inhibiting growth of pathologically proliferating mammalian cells, in a mammal (including humans), or for killing or reducing the growth of mammalian host cells infected with pathologic microbes, comprising administering to said mammal a therapeutic pathologically proliferating mammalian cell or pathologic microbe antiproliferative effective amount of a blocker of the ability of the cells to export nitrosant and of an agent that increases nitrosative stress in the cells. The term "nitrosant" is used here to mean an agent or endogenous species able to deliver $NO^+$, $NO^-$ or $NO_2^+$ group to biological molecules.

Another embodiment herein is directed to a method of inhibiting growth of pathologic microbes or of pathologic helminths or of pathologically proliferating mammalian cells, in a mammal, said method comprising administering to said mammal a pathologic microbe or pathologic helminth or pathologically proliferating mammalian cell antiproliferative effective amount of agent that increases nitrosative stress in said pathologic microbes or in host cells infected with said pathologic microbes or in said pathologic helminths or in said pathologically proliferating mammalian cells whereby nitrosative stress selectively kills or reduces the growth of said microbes or said helminths or said pathologically proliferating mammalian cells or selectively enhances their susceptibility to innate immune defenses or the susceptibility of said microbes to antimicrobial agents (which function by a mechanism other than by manipulating nitrosative stress) or the susceptibility of said helminths to anthelmintic agents (which function by a mechanism other than by manipulating nitrosative stress) or the susceptibility of the pathologically proliferating mammalian cells to antiproliferative agents (which function by a mechanism other than by manipulating nitrosative stress), and also administering to said mammal a hypotensive response preventing or reducing amount of an inhibitor of guanylyl cyclase.

An embodiment of the invention here overlapping some of the embodiments described above and broader than these embodiments in certain respects is a method of inhibiting growth of non-viral pathologic microbes in a mammal (including humans), said method comprising administering to said mammal a pathologic microbe antiproliferative effective amount of a selective inhibitor of thiol synthesis in the microbe to mediate selective killing or growth reduction of said pathologic microbes by agent which is selected from the group consisting of antimicrobials (which are not selective inhibitors of thiol synthesis in the microbe), immune cells in the mammal and products of mammalian antimicrobial response.

Another aspect of the invention is directed to a method of inhibiting growth of pathologic viruses in a mammal (including humans), said method comprising administering to the mammal a non-selective glutathione synthesis inhibitor or glutathione depleter which causes decrease in amount of glutathione in the host cells for the virus and thereby sensitizes the virus to selective killing by antiviral agent, immune cells in the mammal and products of the mammalian antiviral response.

In another embodiment herein, hydroxyurea is administered together with a non-selective glutathione synthesis inhibitor or depleter, e.g., L-buthionine-S-sulfoximine, to treat those disorders now being treated with hydroxyurea without glutathione synthesis inhibitor or depleter.

Another aspect of the invention herein is directed to novel sulfoximines which selectively inhibit glutathione synthesis in glutathione producing microbes, e.g., *E. coli* and Salmonella, when administered to an infected mammal, because they strongly inhibit glutathione synthesis in the glutathione producing microbes but not in mammalian cells. These novel sulfoximines are α-alkyl-S-alkyl-homocysteine sulfoximines wherein the α-alkyl contains 2 to 8 carbon atoms and the S-alkyl contains 1 to 10 carbon atoms. Some examples of species of this genus are α-ethyl-buthionine sulfoximine, α-propyl-buthionine sulfoximine, α-isopropyl-buthionine sulfoximine, and α-tert butyl-buthionine sulfoximine.

We turn now to the invention herein related to treating patients in need of increased nitrosative stress defenses. This can involve manipulating nitrosative stress in a patient to upregulate nitrosative stress defense mechanism in the patient.

One embodiment of this involves a method of treating a mammal in need of increased nitrosative stress defenses and comprises administering to said mammal a nitrosative stress tolerance increasing amount of a manipulator of nitrosative stress to cause increase of nitrosative stress defense mechanism in the mammal.

Another embodiment of this involves a method of treating a mammal, e.g., a human patient, at risk for a cerebral stroke because of having had a transient ischemic attack or a prior stroke comprising upregulating nitrosative stress defense mechanism in said mammal thereby to protect neuronal cells from death from more severe nitrosative stress occurring in the event a cerebral stroke occurs in the mammal.

DETAILED DESCRIPTION

Figure 1:
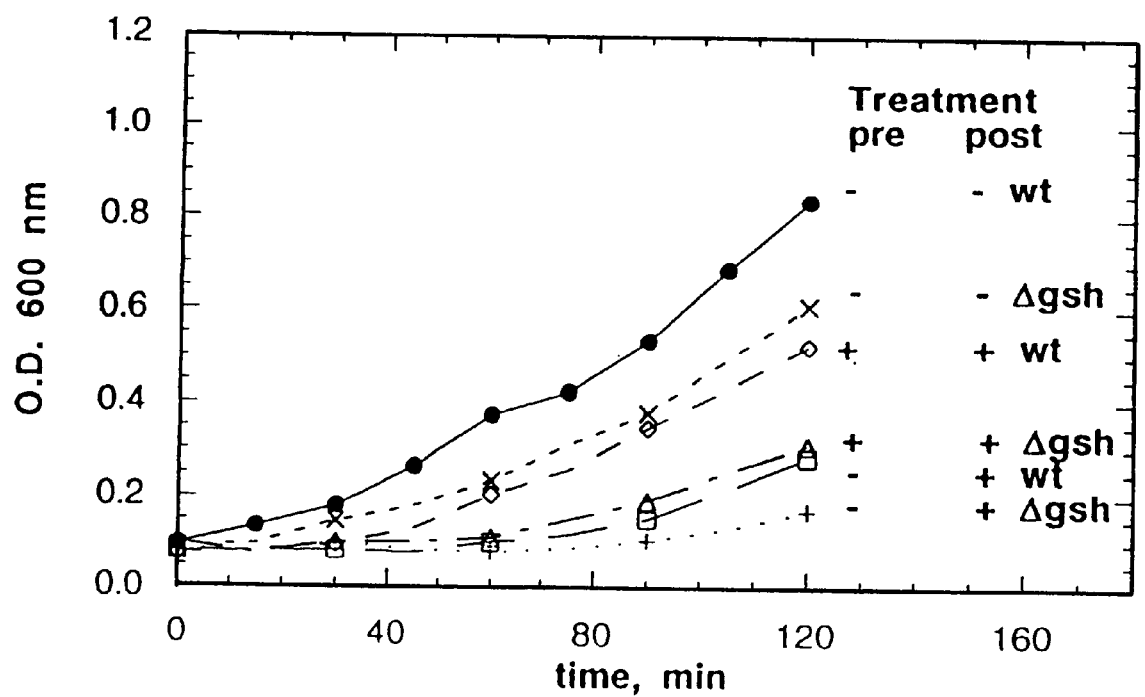
FIG. 1 is a graph where cell density is plotted versus time where O.D. 600 nm is measure of bacterial growth; it graphically depicts results of Example II.

We turn now in more detail to the method of inhibiting growth of pathologic microbes or pathologic helminths or pathologically proliferating mammalian cells, in a mammal, said method comprising administering to said mammal a therapeutic pathologic microbe or pathologic helminth or pathologically proliferating mammalian cell antiproliferative effective amount of at least one manipulator of nitrosative stress in said microbes or in mammalian host cells infected with said microbes or in said helminths or in said pathologically proliferating mammalian cells whereby nitrosative stress selectively kills or reduces the growth of said microbes or helminths or mammalian cells or selectively enhances their susceptibility to innate immune defenses or the susceptibility of said microbes to antimicrobial agents or the susceptibility of said helminths to anthelmintic agents or the susceptibility of said pathologically proliferating mammalian cells to antiproliferation agents; provided that when the pathologically proliferating mammalian cells are those that would cause restenosis, the manipulator of nitrosative stress comprises an inhibitor of protection against nitrosative stress and is employed to selectively kill or reduce the growth of said cells or to enhance their susceptibility to antiproliferation agents. As indicated above, the term "pathologic microbes" as used herein includes pathologic bacteria. The pathologic bacteria, the growth of which are inhibited by methods herein (with some of pathologic conditions which may be treated by the growth inhibiting set forth in parentheses) include, for example, *E. coli* (gastrointestinal distress, sepsis, pneumonia, urinary tract infection, meningitis), Salmonella (biliary gastrointestinal disease, typhoid fever), Haemophilus (influenza, meningitis, upper respiratory diseases, ear infections), *Helicobacter pylori* (ulcers), Mycobacteria (tuberculosis, leprosy), *Borrelia burgdorferi* (Lyme disease), *Staphylococcus aureus* (pneumonia, endocarditis), Gram-negative rods including Klebsiella and Pseudomonas (pneumonia and bacteremia), Pneumococcus (pneumonia, secondary sepsis), *Treponema pallidum* (syphilis), Gonococci (gonorrhea), Actinomycetes (nosocomial infections), Streptomycetes (mycetoma), and *Legionella pneumophila* (Legionaire's disease).

As indicated above, the term "pathologic microbes" as used herein includes pathologic viruses. Pathologic viruses, the growth of which is inhibited by methods herein, and pathologic conditions associated therewith treated by methods herein include, for example, human immunodeficiency virus (AIDS, Kaposi's sarcoma), herpes virus (herpetic infections), cytomegalovirus (pneumonia, CMV mononucleosis), Epstein-Barr virus (infectious mononucleosis Burkitt's lymphoma), hepatitis viruses A, B and C (hepatitis), and rotavirus (viral gastroenteritis).

As indicated above, the term "pathologic microbes" as used herein includes pathologic Chlamydia. Pathologic Chlamydia, the growth of which are inhibited by methods herein, and the conditions associated therewith treated by methods herein include, for example, *C. trochomatis* (genital infections, conjunctivitis, pneumonia), *C. psittaci* (psittacosis).

As indicated above, the term "pathologic microbes" as used herein includes pathologic protozoa. Pathologic protozoa, the growth of which are inhibited by methods herein, and pathologic conditions associated therewith, include, for example, Plasmodii species (malaria), Pneumocystis species (pneumonia), the Kinetoplastida which include Trypanosoma species including *Trypanosoma cruzi* (Chagas' disease), and *Trypanosoma brucei* (African sleeping sickness in humans and nagana in cattle); Leishmania species including *Leishmania donovani* (visceral leishmaniasis or kala azar) and *Leishmania braziliensis* (mucotaneous leishmaniasis or espundia); *Entamoeba histolytica* (amebiasis); and *Giardia lamblia* (giardiasis).

As indicated above, the term "pathologic microbes" as used herein includes pathologic rickettsia. Pathologic rickettsia, the growth of which are inhibited by methods herein, and pathologic conditions associated therewith, include, for example, *R. ricketsii* (Rocky Mountain Spotted fever), *R. typhi* (typhus) and *Ehrlichia canis* (human Ehrlichiosis).

As indicated above, the term "pathologic microbes" as used herein includes pathologic fungi. Pathologic fungi, the growth of which are inhibited by methods herein, and pathologic conditions associated therewith, include Cryptococci species (cryptococcoses including meningitis), Candida species (vaginitis, thrush), and *Aspergillus fumigatus* (aspergillosis).

As indicated above, the term "pathologic microbes" as used herein includes pathologic mycoplasmata. Pathologic mycoplasmata, the growth of which are inhibited by methods herein, and pathologic conditions associated therewith, include, for example, *Mycoplasma homines* (genital tract infections), and *Mycoplasma pneumoniae* (pneumonia).

As indicated above, the term "pathologic helminths" as used herein includes pathologic nematodes, pathologic trematodes and pathologic cestodes. Pathologic helminths, the growth of which are inhibited by methods herein, and the pathologic conditions associated therewith, include, for example, *Ascaris lumbricoides* (roundworm infection), *Necator americanus* (hookworm infection), *Ancylostoma duodenale* (hookworm infection), *Trichinella spiralis* (trichinosis), *Schistosoma haematobium* (schistomiasis), *Schistosoma mansoni* (schistomiasis), *Schistosoma japonicum* (schistomiasis), and *Enterobius vermicularis* (pinworm infection).

The term "pathologically proliferating mammalian cells" as used herein is defined above. It includes, for example, pathologically proliferating cancer cells, the pathologically proliferating or enlarging cells causing restenosis, the pathologically proliferating or enlarging cells causing benign prostatic hypertrophy, the pathologically proliferating cells causing myocardial hypertrophy and proliferating cells at inflammatory sites such as synovial cells in arthritis. Pathologically proliferating cancer cells include the cell proliferation in Hodgkin's disease, in small cell lung cancer, in cancer of the breast, and in testicular and prostate cancer.

The manipulators of nitrosative stress include agents that selectively inhibit protection against nitrosative stress in the pathologic microbes or in mammalian host cells infected with said microbes or in the pathologic helminths, or in the pathologically proliferating mammalian cells, and agents that selectively increase nitrosative stress in the pathologic microbes or in mammalian host cells infected with said microbes or in the pathologic helminths or in the pathologically proliferating mammalian cells, with selectivity occurring because of specific effect either (a) because of greater effect on the pathologic microbes, infected host cells, pathologic helminths or pathologically proliferating mammalian cells than on other cells either because of more specific application or action or because of coaction with drug that has more specific application or action, or (b) because of local delivery. The selective inhibitors of protection against nitrosative stress in the pathologic microbes or in mammalian host cells infected with the pathologic microbes or in the pathologic helminths or in the pathologically proliferating mammalian cells include, for example, selective inhibitors of thiol synthesis or selective depleters of thiol in the pathologic microbes or in the pathologic helminths or in mammalian host cells infected with pathologic microbes in the pathologic helminths or in the pathologically proliferating mammalian cells, selective inhibitors of transcription or translation of an antinitrosative stress gene in the pathologic microbes or in mammalian host cells infected with pathologic microbes or in the pathologic helminths or in the pathologically proliferating mammalian cells and selective inhibitors of an antinitrosative stress gene product in the pathologic microbes or in mammalian host cells infected with pathologic microbes or in the pathologic helminths or in the pathologically proliferating mammalian cells.

In general, the dosage, i.e., the antiproliferative effective amount, ranges from 1 μg to 10 g/kg and often ranges from 10 μg to 1 g/kg or 10 μg to 100 mg/kg body weight of the mammal being treated, per day.

The preferred route of administration in respect to inhibiting growth of microbes is oral administration although other routes of administration including parenteral and topical are useful. Topical administration is especially useful for exposed infections, e.g., fungal infections such as athlete's foot, viral infections such as herpes and microbe-caused oral or skin lesions. For inhibiting the growth of helminths, the preferred route of administration is oral administration although other routes of administration including parenteral are useful. For inhibiting the growth of pathologically proliferating cancer cells, the route of administration can be oral (for example, in the case where the manipulator of nitrosative stress is derivatized from a drug that is administered orally) and can be parenteral (for example, in the case where the manipulator of nitrosative stress is derivatized from a drug that is administered parenterally) and local administration is possible, for example, by infusion directly into a tumor or into the blood vessels delivering blood to the tumor, or by forming the agent into a slow release pellet or into a polymer matrix and then implanting the pellet or polymer matrix device in the tumor. The preferred routes of administration in the case of inhibiting growth of pathologically proliferating mammalian cells that would cause restenosis is from attachment on a stent emplaced in angioplasty. The preferred route of administration in the case of inhibiting growth of pathologically proliferating mammalian cells causing benign prostatic hypertrophy is from attachment on a prostatic implant or by local injection.

We now turn to cases where the manipulator of nitrosative stress is a selective inhibitor of protection against nitrosative stress in the pathogenic microbes or in mammalian host cells infected with pathologic microbes or in the pathologic helminths or in the pathologically proliferating mammalian cells, which is a selective inhibitor of thiol synthesis or selective depleter of thiol in the pathologic microbes or in the host cells or in the pathologic helminths or in the pathologically proliferating mammalian cells. The terms "selective inhibitor of thiol synthesis" and "selective depleter of thiol" apply to agents which selectively inhibit protection against nitrosative stress in pathologic microbes or in host cells infected with pathologic microbes or in the pathologic helminths or in pathologically proliferating mammalian cells, with selectivity occurring because of specific effect either (a) because of greater effect on the pathologic microbes, infected host cells, pathologic helminths or pathologically proliferating mammalian cells than on other cells either because of more specific application or action or because of coaction with drug that has more specific application or action, or (b) because of local delivery.

In general, the antiproliferative effective amount for selective inhibitors of thiol synthesis and selective depleters of thiol in the pathologic microbes or in mammalian host cells infected with the pathologic microbes or in the pathologic helminths or in the pathologically proliferating mammalian cells, i.e., the dosage of selective inhibitor of thiol synthesis or selective depleter of thiol administered to the mammal being treated ranges from 1 μg to 10 g per kg and often ranges from 10 μg to 1 g/kg or 10 μg to 100 mg/kg of mammal's body weight per day.

Thiols and organisms which they protect from nitrosative stress include, for example, glutathione in mammals and helminths and glutathione-producing microorganisms (including glutathione-producing bacteria, such as *E. coli* and Salmonella); trypanothione in trypanosomas, L-homocysteine in *Salmonella typhimurium* and other bacteria containing L-homocysteine; mycothiol in mycothiol-producing microorganisms (including mycothiol-producing bacteria, such as actinomycetes (which cause, for example, mycobacteria tuberculosis), *Nocardia asteroides, Nocardia brasiliensis* and other Nocardia species (which cause, for example, pulmonary nocardiosis), and *Corynebacterium diphtheriae* (which causes diphtheria); ovothiols including ovothiol A in *Leishmania donovani* (which causes visceral Leishmaniases) and ovothiol B and ovothiol C; and the tripeptide δ-(L-α-aminoadipyl)-L-cysteinyl-D-valine in certain Streptomycetes.

Selective inhibitors of thiol synthesis useful herein, include, for example, selective inhibitors of glutathione synthesis in pathologic microbes or in host mammalian cells infected with pathologic microbes or in pathologic helminths or in pathologically proliferating mammalian cells, inhibitors of trypanothione synthesis, inhibitors of L-homocysteine synthesis, inhibitors of mycothiol synthesis, inhibitors of the synthesis of ovothiols, and inhibitors of synthesis of δ-(L-α-aminoadipoyl)-L-cysteinyl-D-valine.

Selective depleters of thiol useful herein, include, for example, selective glutathione depleters, trypanothione depleters, L-homocysteine depleters, mycothiol depleters, and δ-(L-α-aminoadipoyl)-L-cysteinyl-D-valine depleters.

As indicated above, glutathione protects against nitrosative stress in mammals and helminths and glutathione-producing microbes, for example, *E. coli* and Salmonella. Glutathione is also involved in the synthesis of the thiol trypanothione which as indicated above protects against nitrosative stress in trypanosomas. Thus, selective inhibitors of glutathione synthesis and selective depleters of glutathione are administered herein to inhibit growth (proliferation) of glutathione-producing microbes and trypanothione-producing microbes in mammals, e.g., *E. coli* in mammals with *E. coli* caused infections and Salmonella in mammals with Salmonella caused infections and trypanosomas in mammals with trypanosome-caused infections, and to inhibit growth of pathologically proliferating mammalian cells in mammals.

In general, the antiproliferative effective amount administered to a mammal (i.e., the dosage for use herein) of selective inhibitor of glutathione synthesis or of selective depleter of glutathione ranges from 1 μg to 10 g per kg, often 10 μg to 1 g per kg or 10 μg to 100 mg per kg of mammal's body weight per day. The route of administration for selective inhibitor of glutathione synthesis and selective depleter of glutathione is preferably oral although other routes of administration, e.g., parenteral, are also useful.

Selective inhibitors of glutathione synthesis for use in treating infections caused by glutathione-producing microbes are preferably selective inhibitors of microbial gamma-glutamylcysteine synthetase, i.e., compounds which strongly inhibit microbial gamma-glutamylcysteine synthetase but are much weaker inhibitors than L-buthionine-S-sulfoximine of mammalian gamma-glutamylcysteine synthetase which is different chemically from microbial gamma-glutamylcysteine synthetase.

The selective inhibitors of microbial gamma-glutamylcysteine synthetase include, e.g., α-alkyl-S-alkyl-homocysteine sulfoximines (especially the corresponding DL,RS compounds and the L,S-diastereomers) where the α-alkyl contains 2 to 8 carbon atoms and the S-alkyl contains 1 to 10 carbon atoms.

The α-alkyl-S-alkyl-homocysteine sulfoximines can be prepared by reacting alkyl thiol (where the alkyl provides the S-alkyl) and alkyl vinyl ketone (where the alkyl provides the α-alkyl) to form $R_1SCH_2CH_2COR_2$ (where $R_1$ provides the S-alkyl and $R_2$ provides the α-alkyl), reacting that product with ammonium carbonate and sodium cyanide to form the corresponding hydantoin, hydrolyzing the hydantoin to form S-alkyl-α-alkyl-DL-homocysteine and converting that compound to the corresponding sulfoximine by reaction with sodium azide in sulfuric acid/chloroform by the general method described in Griffith, O. W., et al., Meth. Enzymol. 143, 286–291 (1987). To obtain pure L,S-compound, the final product can be fractionated chromographically as described in Griffith, O. W., et al., Meth. Enzymol. 143, 166–172 (1987) or the compound can be fractionally crystallized by following the general procedures described in Campbell, E. B., et al., Anal. Biochem. 194, 268–277 (1991).

There are also many procedures well-known in the art for making α-amino acids which can be applied either to L-methionine to form α-alkyl methionine or to an S-alkyl-homocysteine (e.g., L-buthionine) to form an α-alkyl-S-alkyl-homocysteine. See, for example, *Chemistry of the Amino Acids*, J. P. Greenstein and M. Winitz, Eds., Vol. 3, pp 2559–2579 (1961); J. Org. Chem. 42, 2639–2641 (1977); Tetrahedron Lett. 25, 4337–4340 (1984); Tetrahedron Lett. 25, 1789–1792 (1984) ; Tetrahedron Lett. 32, 2999–3002 (1979); and Angew. Chem. Int. Ed. Engl. 17, 117–119 (1978). α-Alkyl-S-alkyl-homocysteines can be converted to the corresponding sulfoximines by the general procedures described in Griffith, O. W., J. Biol. Chem. 257, 13704–13712 (1982) or by the method of Johnson, C. R., et al., J. Org. Chem. 39, 2458–2459 (1974). References cited in this paragraph document standard procedures for obtaining the L-enantiomers of α-alkyl amino acids.

A preferred selective inhibitor of glutathione synthesis within the above-described genus is α-ethyl-L-buthionine-S-sulfoximine, which can be readily prepared by the method described above, i.e., by reacting butanethiol with ethyl vinyl ketone to form $CH_3(CH_2)_3SCH_2CH_2COCH_2CH_3$, reacting that product with ammonium carbonate and sodium cyanide to form the corresponding hydantoin, hydrolyzing the hydantoin in alkali to form α-ethyl-DL-buthionine, converting that compound to the corresponding sulfoximine by reaction with sodium azide in sulfuric acid/chloroform, and isolating the L,S-diastereomer if desired. The D,L-R,S-compound can be used for the L,S-diastereomer present therein, without isolation of the L,S-diastereomer, if desired.

Other sulfoximines embraced by the genus described above, include, for example, α-propyl-DL-buthionine-SR-sulfoximine, α-isopropyl-DL-buthionine-SR-sulfoximine, α-butyl-DL-buthionine-SR-sulfoximine, α-tert butyl-DL-buthionine-SR-sulfoxime, α-ethyl-S-butyl-δ-thionorvaline sulfoximine, and α-propyl-S-butyl-δ-thionorvaline sulfoximine. Also useful are the corresponding ethyl esters of these compounds, the corresponding isopropyl esters of these compounds, the corresponding N-α-acetylated derivatives of these compounds and the corresponding compounds which are both N-α-acetylated and esterified.

The antiproliferative effective amount (i.e., the dosage) for the sulfoximines described above generally ranges from 1 μg to 10 g per kg, often 10 μg to 1 g per kg or 10 μg to 100 mg per kg of mammal body weight per day. The route of administration for the unesterified sulfoximines is preferably oral although other routes of administration, e.g., parenteral or topical, are also useful. The route of administration for the esterified sulfoximines is preferably intravenous but other routes of administration, e.g., topical, are also useful. Oral administration is typically unuseful for the esterified derivatives. Transport of the unesterified amino acids across the blood brain barrier for treatment of microbial infections in the brain is limited whereas transport of esterified amino acids across the blood brain barrier for treatment of microbial infections in the brain is adequate to treat brain infections or lesions. Unesterified α-alkyl-S-alkyl-homocysteine sulfoximines are preferred when the route of administration is oral and esterified α-alkyl-S-alkyl-homocysteine sulfoximines are preferred when the route of administration is intravenous and the compound is given for treatment of infections of the brain.

Other selective inhibitors of glutathione synthesis for use in treating infections caused by glutathione-producing microbes include, for example, 2-amino-2-alkyl-4-oxo-5-chloropentanoic acid where the 2-alkyl group contains 1 to 6 carbon atoms and preferably contains 2 carbon atoms, 2-alkyl-4-methylene-D-glutamic acid where the 2-alkyl group contains 1 to 6 carbon atoms and preferably contains 2 carbon atoms and S-alkyl-D-homocysteine sulfoximines where the alkyl group contains 1 to 10 carbon atoms (e.g., D-buthionine sulfoximine). The S-alkyl-D-homocysteine sulfoximines are selective inhibitors of glutathione synthesis in bacteria containing amino acid racemases able to convert these compounds to a mixture of D and L-compounds in which the L-compound will be pharmacologically active; mammalian cells do not contain amino acid racemases. Each of the inhibitors listed in this paragraph is administered at a dose such that pharmacologically active concentrations are reached in the tissue, biological fluid, or cell space infected by the microorganisms; typically doses of 10 μg to 100 mg/kg body weight per day are appropriate. The compounds can be administered either orally or parenterally, for example, by intravenous administration.

It is noted that the gamma-glutamylcysteine synthetase for trypanosomes is different from mammalian gamma-glutamylcysteine synthetase. Therefore inhibition of trypanosome gamma-glutamylcysteine synthetase with sulfoximine analogues that do not inhibit mammalian gamma-glutamylcysteine synthetase will selectively inhibit the growth and proliferation of trypanosomes when administered to mammals infected with trypanosomes.

Selective inhibitors of glutathione synthesis for use in treating helminth caused infections include, for example, antihelminth antibody cross-linked by ester linkage to thiol synthesis inhibitor such as L-buthionine-S-sulfoximine. The antiproliferative effective amount, i.e., the dosage normally ranges from 1 μg to 10 g/kg, often 10 μg to 1 g/kg or 10 μg to 100 mg/kg of mammalian body weight per day. The route of administration is preferably intravenous.

Selective depleters of glutathione for use in treating infections caused by glutathione-producing microbes include, for example, transportable nitrosylated peptides, e.g., serinyl-S-nitrosylcysteinyl-glutamine. The antiproliferative effective amount (i.e., the dosage) for these compounds normally ranges 10 μg to 100 mg per kg of mammal body weight per day. The route of administration is preferably intravenous.

Selective depleters of glutathione synthesis for use in treating helminth caused infections include, for example, antihelminth antibody cross-linked by ester linkage to ethyl maleate. Such compounds are preferably administered intravenously at a dosage of 10 μg to 100 mg/kg mammalian body weight per day.

Selective inhibitors of glutathione synthesis for use in inhibiting proliferation of pathologically proliferating cancer cells, include, for example, an antitumor antibody (i.e., to an epitope on a cancer cell) cross-linked by ester linkage to thiol synthesis inhibitor such as L-buthionine-S-sulfoximine. The antiproliferative effective amount, i.e., the dosage, normally ranges from 1 μg to 10 g/kg, often 10 μg to 1 g per kg or 10 μg to 100 mg per kg of mammal body weight. The route of administration is preferably intravenous.

Selective depleters of glutathione for use in inhibiting proliferation of pathologically proliferating cancer cells, include, for example, an antitumor antibody (i.e., to an epitope on a cancer cell) cross-linked by ester linkage to ethyl maleate. Such compounds are preferably administered intravenously at a dosage of 10 μg to 100 mg/kg mammalian body weight per day.

Inhibitors of glutathione synthesis for use in inhibiting proliferation of pathologically proliferating cells that would cause restenosis include, for example, non-selective inhibitor of glutathione synthesis, e.g., L-buthionine-S-sulfoximine attached to a stent, optionally used in combination with administration of intravascular beta-, gamma- or X-ray radiation. Specific embodiments include L-buthionine-S-sulfoximine attached to a polymer stent by ester linkage in which case it is released by extracellular esterases, or incorporating L-buthionine-S-sulfoximine into a porous polymer stent from which it slowly diffuses once the stent has been placed in the occluded artery. In these cases, appropriate dosing requires that the stent incorporate 0.1 to 10% L-buthionine-S-sulfoximine by weight of the polymer used in the stent. The route of administration is local. Intravascular beta- or gamma-radiation is optionally applied, for example, by using a Palaz-Schatz Stent implanted with radioactive $^{32}$p , e.g., at a dosage of 0.1 μCi, or $^{192}$Ir, e.g., at a dosage ranging from 350–2500 cGy, preferably at a dosage greater than 1400 cGy, or $^{90}$Sr/Y, e.g., at a dosage ranging from 7–56 Gy.

Depleters of glutathione for use in inhibiting proliferation of pathologically proliferating cells that would cause restenosis include, for example, ethyl maleate attached to polymer stent by ester linkage or ethyl maleate agent incorporated into a porous polymer stent such that it slowly diffuses from the polymer stent emplaced in an occluded artery. Other useful agents include agents causing overexpression of transaldolase, e.g., transaldolase increasing genetic vectors such as a construct containing antisense to promoter of human transaldolase, attached to a polymer stent or incorporated into a porous polymer stent or administered by a drug delivery balloon at the time of stent placement; these agents inhibit part of the pentose phosphate pathway responsible for NADPH synthesis thereby depriving glutathione reductase of NADPH substrate which prevents reduction of glutathione disulfide back to glutathione and thereby cause glutathione depletion. Nitrosating agents attached to a polymer stent or incorporated into a porous polymer stent contribute both to thiol depletion and to nitrosative stress. For all these drugs, appropriate dosages are 0.1–10% by weight of polymer used in the stent. The route of administration is local.

For inhibiting proliferation of pathologically proliferating cells that would cause restenosis, the rate of drug release should be such that the duration of therapy following implantation of the stent is 1 to 20 days or longer.

Inhibitors of glutathione synthesis for use in inhibiting proliferation of pathologically proliferating cells causing benign prostatic hypertrophy include, for example, L-buthionine-S-sulfoximine attached to a pellet which is implanted in the prostate, e.g., L-buthionine-S-sulfoximine attached to polymer of a polymer pellet by ester linkage or incorporated into a porous polymer pellet from which it slowly diffuses once the pellet is implanted. In these cases, the appropriate dosages are 0.1 to 10% by weight of polymer used in the pellet. The rate of drug release should be such that the duration of drug therapy following implantation of the pellet is 1 to 20 days or longer. The route of administration is local.

Depleters of glutathione for use in inhibiting proliferation of pathologically proliferating cells causing benign prostatic hypertrophy include, for example, ethyl maleate attached to a pellet for implantation into the prostate, e.g., ethyl maleate attached to the polymer of a polymer pellet by an ester linkage or ester maleate incorporated into a porous polymer pellet such that it slowly diffuses from the polymer pellet that has been implanted. Nitrosating agents attached to a polymer pellet or incorporated into a porous polymer pellet contribute both to thiol depletion and to nitrosative stress. For all these drugs, appropriate dosages are 0.1 to 10% by weight of polymer used in the pellet. The rate of drug release should be such that the duration of drug therapy following implantation of the pellet is 1 to 20 days or longer. The route of administration is local.

In other cases for treating mammals to inhibit the growth of pathologically proliferating mammalian cells therein especially for inhibiting the growth of cells that would cause restenosis or for inhibiting the proliferation of cells causing benign prostatic hypertrophy, antitumor alkylator, e.g., melphalan, is administered locally as a mechanism of glutathione depletion in proliferating cells, preferably with co-administration locally of agent that inhibits the synthesis of glutathione, e.g., L-buthionine-S-sulfoximine, with or without co-administration of agent that increases nitrosative stress. For example, the alkylator is associated with polymer in a stent for the inhibition of pathologically proliferating cells that would cause restenosis or with a polymeric pellet for implantation in the prostate for inhibition of proliferation of cells causing benign prostatic hypertrophy and the alkylator is present in an amount of 0.1 to 10% by weight of polymer in the stent or pellet and drug release is such that the therapy continues for 1 to 20 days after insertion of the stent or implantation of the pellet.

As indicated above, L-homocysteine protects against nitrosative stress in *Salmonella typhimurium* and other bacteria producing L-homocysteine. L-Homocysteine does not protect against nitrosative stress in mammals. Thus, inhibitors of bacterial L-homocysteine synthesis and depleters of L-homocysteine are administered herein to selectively inhibit growth (proliferation) of L-homocysteine producing microbes in mammals, e.g., to treat *S. typhimurium* caused infections. Selectively inhibiting bacterial L-homocysteine synthesis or selectively depleting L-homocysteine in L-homocysteine producing microbes can be carried out by administering to the infected mammal agent comprising vector carrying an antisense construct to the MetL gene of Salmonella. While mammals do produce L-homocysteine (by a different pathway of synthesis from bacteria) and while mammalian cells contain trace amounts of L-homocysteine, this agent has no effect on production of L-homocysteine in mammals. The antiproliferative effective amount (dosage) administered ranges from 1 µg to 100 mg/kg mammal body weight per day. The route of administration is preferably intravenous.

Mycothiol (described in Newton, G. L., et al., J. Bacteriol, 178, 1990–1995 (1996)) protects against nitrosative stress in mycothiol-producing microbes, e.g., Mycobacter and Actinomycetes. Mycothiol does not protect against nitrosative stress in mammals. Thus, inhibitors of mycothiol synthesis and depleters of mycothiol are administered herein to selectively inhibit growth (proliferation) of mycothiol-producing microbes in mammals with infections caused thereby.

In general, the antiproliferative effective amount administered to a mammal (i.e., the dosage for use herein) of inhibitor of mycothiol synthesis or of selective depleter of mycothiol ranges from 1 µg to 10 g per kg, often 10 µg to 1 g per kg or 10 µg to 100 mg per kg of mammal body weight per day. The route of administration for inhibitor of mycothiol synthesis and for selective depleter of mycothiol is preferably parenteral, although other routes of administration are also useful.

Inhibitors of mycothiol synthesis and depleters of mycothiol for administration to mammals infected with mycothiol producing microbes include, for example, inhibitors of microbial cysteine biosynthesis or cysteine synthesis antagonists (1,2,4-trazole is described in J. Gen. Microbiol. 72, 291–301 (1972) as inhibiting the growth of S. typhimurium by interference with the induction of cysteine biosynthetic enzymes) and transportable-nitrosylated peptides that are selectively taken up by microorganisms, exemplified, by serinyl-s-nitrosocysteinyl-glutamine. Serinyl-S-nitrosysteinyl-glutamine can be prepared by nitrosylating serinylcysteinylglutamine using acidified sodium nitrite. Serinylcysteinylglutamine is prepared by conventional amino acid synthesis methods including automated syntheses such as are available on commercial instruments. Dosages for the peptides range from 10 µg to 100 mg/kg mammal body weight per day and the route of administration for these is preferably intravenous.

As indicated above, ovothiol A protects against nitrosative stress in *Leishmania donovani* and other microbes producing ovothiol A. Ovothiol A does not protect against nitrosative stress in mammals. Thus, inhibitors of ovothiol synthesis (e.g., ovothiol A synthesis) and depleters of ovothiol (e.g., ovothiol A) are administered herein to selectively inhibit growth (proliferation) of ovothiol producing microbes in mammals, e.g., *L. donovani* in *L. donovani* infected mammals. Ovothiols are more nucleophilic and more reactive towards alkylating agents and oxidants than glutathione and are better free radical scavengers than aliphatic thiols such as glutathione. Thus, selective depletion can be obtained by administering alkylating agents, e.g., melphalan, mechlorethamine, chlorambucil, cyclophosphamide and ifosphamide. The same dosages and routes of administration as used for antineoplastic utility are suitable herein.

δ-(L-aminoadipoyl)-L-cysteinyl-D-valine protects against nitrosative stress in microbes producing this thiol, e.g., Streptomycetes. δ-(L-aminoadipoyl)-L-cysteinyl-D-valine does not protect against nitrosative stress in mammals. Thus, inhibitors of synthesis of δ-(L-aminoadipoyl)-L-cysteinyl-D-valine and depleters of δ-(L-aminoadipoyl)-L-cysteinyl-D-valine (hereinafter sometimes ACV) are administered herein to selectively inhibit growth (proliferation) of ACV-producing microbes in mammals with infections caused thereby. In general, the antiproliferative effective amount (dosage) of inhibitor of ACV synthesis or depleter of ACV ranges from 10 µg to 10 g per kg, often 10 µg to 1 g per kg, or 10 µg to 100 mg per kg of mammal body weight per day and the route of administration for inhibitor of ACV synthesis and for depleter of ACV is preferably oral although other routes of administration, e.g., parenteral, are also useful. Preferred inhibitors of ACV synthesis are S-alkyl-δ-thionorvaline sulfoximines and a preferred member of this genus is δ-butylthio-DL-norvaline-SR-sulfoximine and the dosage for these compounds may range from 10 µg to 10 g per kg, often 10 µg to 1 g/kg or 10 µg to 100 mg/kg of mammal body weight per day and the route of administration for these compounds is preferably oral although other routes of administration, e.g., parenteral, are also useful.

Newton, G. L., et al., J. Bacteriol. 178, 1990–1995 (1996) describes the thiol content of microorganisms and provides a procedure that allows amount of thiol to be monitored. This information allows thiol synthesis inhibiting agents and thiol depleting agents to be selected or tested for use for administration to a mammal for selective killing or reducing the growth of microorganisms infecting the mammal.

We turn now to cases where the manipulator of nitrosative stress is a selective inhibitor of transcription or translation of an antinitrosative stress gene or a selective inhibitor of an antinitrosative stress gene product.

We turn now to the case where an inhibitor of transcription or translation of an antinitrosative stress gene of a pathologic microbe is administered to a mammal infected with the microbe to selectively kill or reduce the growth of the microbe. Where the inhibition is carried out on pathologic microbes whose genome contains OxyR, e.g., *E. coli*, Salmonella and Mycobacterium, a selective inhibitor of transcription or translation of an antinitrosative stress gene is an inhibitor of OxyR transcription or translation. Inhibitors of OxyR transcription or translation are selective because OxyR is not present in mammalian genomes. Inhibitors of OxyR transcription or translation which function as selective inhibitors herein are vectors containing antisense constructs to the OxyR promoter or antisense constructs to the OxyR mRNA or are infusions of reducing agents, such as ascorbate. Said antisense constructs may be prepared by conventional DNA synthesis methods. The vector selected to carry the antisense construct is one known to infect the microbe targeted and, therefore, is a bacteriophage. The bacteriophage delivers the antisense construct into the microbe where it is transcribed into the antisense RNA. The antisense sequence binds to the promoter region of OxyR preventing its transcription into mRNA so that the OxyR gene is effectively turned off or binds to the OxyR mRNA so the synthesis of OxyR protein is turned off. Alternatively, small antisense constructs directed at either the OxyR promoter or OxyR mRNA can be administered directly using various strategies to allow entry into the cell; phosphorthiolate nucleotides and other strategies can be used to minimize hydrolysis of such antisense constructs as described in Crooke, S. T., Hematologic Pathology 9, 59–72 (1995). In general, the antiproliferative effective amount (dosage) for inhibitor of OxyR transcription or translation for administration to infected mammal ranges from 1 µg to 10 g per kg, often 10 μg to 1 g per kg or 10 μg to 100 mg per kg of mammalian body weight per day and the route of administration is preferably oral or intravenous, or vectors carrying the antisense construct are administered intravenously at doses of 10 μg to 1 mg/kg mammalian body weight per day. In one embodiment herein where inhibition of growth is carried out on OxyR-containing microbes infecting a mammal, two kinds of manipulators of nitrosative stress in said microbes are administered to the infected mammal and one kind is an inhibitor of OxyR transcription or translation as described above (with the dosage and route of administration described above) and the other kind is a selective inhibitor of thiol synthesis or depleter of thiol in the infecting microbe (with the dosage and route of administration described above) or a selective increaser of nitrosative stress in microbes (as described below with dosages and routes of administration as described below).

We turn now to the case where a selective inhibitor of an antinitrosative stress gene product of a pathologic microbe is administered to a mammal infected with the microbe to selectively kill or reduce the growth of the microbe. Inhibitors of antinitrosative stress gene products of pathologic microbes which function as selective inhibitors herein are anti-sense constructs to heat shock protein genes which may be prepared by conventional DNA synthesis methods, and a vector to carry the anti-sense construct is one known to infect the microbe targeted. Vectors carrying the anti-sense construct are administered intravenously at doses of 10 μg to 1 mg/kg mammalian body weight per day.

We turn now to the case where a selective inhibitor of transcription or translation of an antinitrosative stress gene of a pathologic helminth is administered to a mammal infected with a pathologic helminth to selectively kill or reduce the growth of the helminth. The inhibitors used for treatment can be, for example, a vector containing an antisense construct to a catalase promoter or mRNA, a vector containing an antisense construct to a heme oxygenase promoter or mRNA or a vector containing an antisense construct to a heat shock protein or mRNA. The inhibitors are made selective, for example, by attachment to antihelminth antibody and are administered intravenously at a dosage of 1 μg to 100 mg.

We turn now to the case where a selective inhibitor of an antinitrosative stress gene product of a pathologic helminth is administered to a mammal infected with the pathologic helminth to selectively kill or reduce the growth of the helminth. The inhibitor is aminotriazole which is made selective by cross-linking by an amide linkage to antihelminth antibody and is administered intravenously at a dosage of 10 μg to 100 mg/kg mammalian body weight per day.

We turn now to the cases where a selective inhibitor of transcription or translation of an antinitrosative stress gene is administered to a mammal to inhibit the proliferation (growth) of pathologically proliferating mammalian cells in the mammal. The inhibitor can be, for example, a vector containing an antisense construct to a catalase promoter or mRNA, a vector containing an antisense construct to a heme oxygenase promoter or mRNA or a vector containing an antisense construct to a heat shock protein promoter or mRNA. For inhibiting proliferation of pathologically proliferating cancer cells, the agents are made selective by local delivery or by attachment to a tumor specific antibody or by other strategies for local delivery well-known in the drug delivery art and are administered intravenously at a dosage of 1 μg to 100 mg. For inhibiting the proliferation of pathologically proliferating cells that would cause restenosis, the agents are made selective by attachment to a polymer stent or by incorporation thereof in a porous polymer stent in an amount ranging from 0.1 to 10% by weight of the polymer in the stent and the rate of drug release should be such that the duration of drug therapy following implantation of the stent is 1 to 20 days or longer. For inhibiting the proliferation of pathologically proliferating cells causing benign prostatic hypertrophy, the agents are made selective by attachment to polymer of a polymer pellet which is implanted into the prostate or by incorporation into a porous polymer pellet from which it slowly diffuses once the pellet is implanted in the prostate. In these cases, the agents are employed in an amount ranging from 0.1 to 10% by weight of the polymer in the pellet and the rate of drug release should be such that the duration of drug therapy following implantation of the pellet is 1 to 20 days or longer.

We turn now to the cases where a selective inhibitor of an antinitrosative stress gene product is administered to a mammal to inhibit the proliferation (growth) of pathologically proliferating mammalian cells in the mammal. The inhibitor can be, for example, aminotriazole which inhibits catalase. Catalase has as a side activity, the ability to convert $NO_2^-$ to $NO_3^-$. Once activated by $H_2O_2$, $NO_2^-$ is a much stronger nitrosating agent than $NO_3^-$. Thus, inhibition of catalase results in stronger nitrosating agent being present. For inhibiting proliferation of pathologically proliferating cancer cells, aminotriazole is made selective by cross-linking by an amide linkage to antitumor antibody (i.e., to an epitope of a cancer cell) and the selective agent is administered intravenously at a dosage of 10 μg to 100 mg/kg mammalian body weight per day. For inhibiting proliferation of pathologically proliferating cells that would cause restenosis, aminotriazole is made selective by attachment (e.g., by amide linkage) to polymer of a polymer stent or by incorporation into a porous polymer stent in an amount ranging from 0.1 to 10% by weight of the polymer in the stent and the rate of drug release should be such that the duration of drug therapy following implantation of the stent is 1 to 20 days or longer. For inhibiting the proliferation of pathologically proliferating cells causing benign prostatic hypertrophy, aminotriazole is made selective by attachment to polymer (e.g., by amide linkage) of a polymer pellet which is implanted into the prostate or by incorporation into a porous polymer pellet from which it slowly diffuses once the pellet is implanted into the prostate. In these cases, the aminotriazole is employed in an amount ranging from 0.1 to 10% by weight of the polymer in the pellet, and the rate of drug release should be such that the duration of therapy following implantation of the pellet is 1 to 20 days.

Another example of an inhibitor of an antinitrosative stress gene product for administration to a mammal to inhibit the proliferation (growth) of pathologically proliferating cells in the mammal is an inhibitor of heme oxygenase, e.g., tin protoporphyrin IX and zinc protoporphyrin IX. These compounds are made selective by local delivery or, in the case of proliferating cancer cells, by attachment to a tumor specific antibody. In the former case, they may be administered from a stent or an implant pellet where they are present in an amount ranging from 0.1 to 10% by weight of the polymer in the stent or pellet and the rate of release is such that duration of drug therapy following implantation is 1 to 20 days or longer. In the latter case, administration is preferably intravenous at a dosage of 1 μg to 100 mg/kg mammalian body weight per day.

In one embodiment herein, the selective inhibitors of protection against nitrosative stress in application to killing microbes or helminths are administered in combination with cytokines which activate immune cells to kill microbes or helminths. These cytokines include, for example, tumor necrosis factor, interleukin-1, interleukin-2, and interferon-gamma. Dosages for the cytokines are in the range of 0.01 μg to 100 μg/kg body weight and administration is intravenous.

The inventions herein do not include inhibiting the growth of proliferating mammalian cancer cells by administering an inhibitor of protection against nitrosative stress which is not itself selective for the proliferating cancer cells, e.g., L-buthionine-S-sulfoximine, and also anticancer agent that inhibits proliferation of mammalian cancer cells by a mechanism other than by manipulating nitrosative stress, without administration of agent that increases nitrosative stress.

We turn now to cases where the manipulator of nitrosative stress is an agent that selectively increases nitrosative stress in pathologic microbes or in pathologic helminths or in pathologically proliferating mammalian cells.

We turn now to the case where the agent that selectively increases nitrosative stress is one that is to be administered to a microbe-infected mammal to inhibit growth of the microbe in the mammal.

In one case of this kind, the agent is one that selectively delivers nitrosating agent, i.e., agent that releases $NO^+$, $NO^-$ or $NO_2^+$ group, to the microbe. An agent of this kind is antibiotic or drug that kills or reduces growth of infecting microbes, substituted to transfer $NO^+$, $NO^-$ or $NO_2^+$ group to the microbes on being metabolized or taken up by the microbes.

Many antibiotics are taken up by all cells, both mammalian and microbial. Nonetheless, there is selectivity for microbial killing because the antibiotic and nitrosating agent act synergistically in the microbes to cause killing, whereas in normal mammalian cells, the antibiotic has no cell killing effect and therefore there is no synergy with the nitrosating agent.

On the other hand, there are some antibiotics that are selectively taken up into microbes. For example, quinine, a drug used against the malaria parasite *P. fulciparum*, is highly concentrated in the acidic food vacuoles of that parasite. Metronidazole, used against Bacteroids, Clostridium and Heliobacter species, is selectively toxic to these anaerobic or microaerophilic microorganisms because it is in these environments that it is reductively activated. Sodium stibogluconate used to treat *L. donovoni* infections in hamsters is selectively taken up by endocytosis to reach the phagolysosomes of macrophages where parasites reside. A number of anti-viral nucleoside drugs such as zidovudine (AZT), acyclovir, penciclovir, and the prodrug famciclovir are concentrated in virus-infected cells by virtue of an initial phosphorylation that requires a viral rather than a mammalian enzyme.

The antibiotics (including antivirals) and drugs which are substituted to contain moiety that transfers $NO^+$, $NO^-$ or $NO_2^+$ group to infecting microbes can be made from antibiotics and drugs which are not so substituted, for example, by conversion of hydroxy groups with NO to nitrite esters or with $NO_2$ to nitrate esters, by substitution of a primary or secondary amino group with a hydroxy acid (e.g., glycolic acid) followed by conversion of the hydroxy groups to nitrite esters and nitrate esters, by conversion of a secondary amino function to a NONOate species which release NO, some fraction of which would be expected to be converted to nitrosating agent in vivo, by conversion of thiol groups to S-nitrosothiols, e.g., by treatment with acidified sodium nitrite, and by substitution of primary and secondary amino groups or hydroxyl groups with a thiol acid (e.g., thiolacetic acid) to give the corresponding amide or ester and provide a thiol group which is converted to S-nitrosothiol group as described above. For peptide antibiotics that do not contain cysteine residues, it is possible to replace valine or alanine residues with cysteine with a high expectation that antibiotic activity will not be affected and then to convert the thiol moiety to S-nitrosothiol as described above. For other kinds of derivatives that generate nitrosating species, see the chapter by M. Feelish and J. S. Stamler entitled "Donors of Nitrogen Oxides" in Methods in Nitric Oxide Research (M. Feelish and J. S. Stamler, eds.). John Wiley & Sons, Chichester, England (1991), pp. 71–115, which is incorporated herein by reference.

Drugs substituted to transfer $NO^+$, $NO^-$ or $NO_2^+$ group to infecting microbes include, e.g., NO-substituted isoniazid, NO-substituted rifampin, NO-substituted halofantrine, NO-substituted mefloquine, NO-substituted primaquine, NO-substituted clindamycin, NO-substituted penicillins, NO-substituted cephalosporins, NO-substituted quinolones, NO-substituted quinine, NO-substituted metronidazole, nitrite and nitrite esters of sodium stibogluconate, and NO-substituted antivirals.

Another agent of the kind that selectively delivers nitrosating agent to microbes that is administered to a microbe-infected mammal to inhibit growth of the microbe in the mammal is substrate for nitrate or nitrite reductase or nitrogen oxide substrate for sulfite metabolizing enzyme or is organic or inorganic nitrate or nitrite that selectively delivers nitrosating agent to the microbes, and includes, for example, sodium nitrate, sodium nitrite, calcium nitrate, calcium nitrite and transition metal-NO complexes.

Still another agent of the kind that selectively delivers nitrosating agent to microbes that is administered to a microbe-infected mammal to inhibit growth of the microbe in the mammal is agent selected from the group consisting of S-nitroso-gamma-methyl-L-homocysteine, S-nitroso-L-homocysteine, S-nitroso-gamma-thio-L-leucine, S-nitroso-δ-thio-L-leucine and tripeptides in which two of the residues are selected from the group consisting of serine, glutamine, alanine, leucine, and methionine, and the other residue is S-nitrosocysteine. These are S-nitroso containing compounds based on peptides or amino acids known to be taken up by microbes. S-Nitroso-gamma-methyl-L-homocysteine can be prepared by reacting gamma-methyl-L-homocysteine with acidified sodium nitrite; gamma-methyl-L-homocysteine can be prepared by sodium/liquid ammonia cleavage of the S-methyl group from gamma-methyl-L-methionine, the synthesis of which is well known in the art. S-Nitroso-L-homocysteine can be prepared by reaction of L-homocysteine with acidified sodium nitrite. S-Nitroso-gamma-thio-L-leucine can be prepared by reacting gamma-thio-L-leucine with acidified sodium nitrite; gamma-thio-L-leucine can be prepared by conventional Strecker amino acid synthesis from S-benzyl-β,β-dimethyl-β-thiopropionaldehyde followed by reductive removal of the S-benzyl group using sodium in liquid ammonia and resolution of the D,L racemate by established procedures (e.g., by acetylation of the amino group and selective cleavage of the L-enantiomer using kidney acylase). S-Benzyl-β,β-dimethyl-β-thiopropionaldehyde is prepared by addition of benzyl mercaptan to β,β-dimethylacrylaldehyde. S-Nitroso-δ-thio-L-leucine can be prepared by reacting δ-thio-L-leucine with acidified sodium nitrite. δ-Thio-L-leucine can be prepared by reacting diethylacetamidomalonate with S-benzyl-α-methyl-β-thiopropyl bromide followed by acid hydrolysis of the ethyl esters and acetamido group and spontaneous decarboxylation of the resulting α-substituted malonic acid. The S-benzyl group is reductively removed using sodium and liquid ammonia and the D,L-racemate is resolved by established procedures as described for gamma-thio-L-leucine. The required S-benzyl-α-methyl-β-thiopropyl bromide is synthesized by reacting excess 1,3-dibromo-α-methyl propane with benzyl mercaptan. The tripeptides in which two of the residues are selected from the group consisting of serine, glutamine, alanine, leucine, and methionine and the other residue is S-nitrosocysteine can be prepared in un-nitrosolated form, for example, by conventional peptide synthesis procedures well established in the art including use of automated peptide synthesis instruments and then S-nitrosolated using acidified sodium nitrite.

Dosage for the antibiotics and drugs substituted to transfer $NO^+$, $NO^-$ or $NO_2^+$ group on being metabolized by or transported into the infecting microbe, is preferably the same as for the same antibiotic or drug without substitution to transfer $NO^+$, $NO^-$ or $NO_2^+$ group on being metabolized by or transported into the infecting microbe except that in cases where NO-substitution reduces the inherent microbe inhibiting efficacy of the antibiotic or drug, the NO-substituted drug is administered at a higher dose so as to attain or exceed the original microbe inhibiting efficacy. The route of administration for the substituted antibiotics and drugs is preferably the same as for the antibiotics and drugs without substitution to transfer $NO^+$, $NO^-$ or $NO_2^+$ group on being metabolized by or transported into the infecting microbe. Dosage for agents that are substrates for nitrate or nitrite reductase or nitrogen oxide substrate for sulfite metabolizing enzyme or that are organic or inorganic nitrates or nitrites that selectively deliver nitrosating agent to the infecting microbes generally ranges from 10 $\mu$g to 100 mg per kg of mammal body weight per day and the route of administration is preferably intravenous although other routes of administration, e.g., other parenteral and topical, also are useful. Dosages for S-nitroso-gamma-methyl-L-homocysteine, S-nitroso-L-homocysteine, S-nitroso-gamma-thio-L-leucine and S-nitroso-δ-thio-L-leucine and for the tripeptides in which two of the residues are selected from the group consisting of serine, glutamine, alanine, leucine and methionine and the other residue is S-nitrosocysteine, in general range from 10 $\mu$g to 100 mg per kg mammalian body weight per day. The route of administration for the non-peptide nitrosothiols is preferably oral or intravenous although parenteral routes of administration in addition to intravenous or topical administration can also be appropriate. For the tripeptides, the route of administration is preferably intravenous. For the tripeptides, oral administration is not appropriate except in the case of infections of the gastrointestinal tract since the tripeptides would be digested in the gastrointestinal tract, and therefore, in most cases of orally administered compounds would not be absorbed as intact peptides. For the tripeptides, other parenteral routes in addition to intravenous and topical administration can also be appropriate.

We turn now to the cases where the agent that selectively increases nitrosative stress is to be administered to a helminth infected mammal to inhibit growth of the helminth in the mammal.

In one case of this kind, nitrosating agent, preferably S-nitrosothiol, is administered with anthelmintic agent that kills or reduces the growth of infecting helminth and functions by a mechanism other than by manipulating nitrosative stress. Selectivity is present because there is synergy between the activity of the anthelmintic agent and the additional toxicity of nitrosative stress that provides a selective effect. Examples of S-nitrosothiols include S-nitrosoglutathione, S-nitroso-N-acetylpenicillamine, S-nitrosocysteine, S-nitroso-gamma-methyl-L-homocysteine, S-nitroso-L-homocysteine, S-nitroso-gamma-thio-L-leucine and S-nitroso-δ-thio-L-leucine. The anthelmintic agents are those used for the type of helminth infection being treated and include, for example, pyrantel pamoate, mebendazole, praziquantel, oxamniquine, metrifonate, thiabendazole, and niclosamide. The nitrosating agent is preferably administered orally although other routes of administration, e.g., parenteral including intravenous are also useful. The dosage for the nitrosating agent is 1 $\mu$g to 10 gm/kg and often 10 $\mu$g to 1 gm/kg or 100 $\mu$g to 100 mg/kg body weight per day. The anthelmintic agents are used with the same dosages and routes of administration as are employed when treatment with nitrosating agent is omitted.

In another case of this kind, the agent is anthelmintic agent that kills or reduces the growth of infecting helminth, substituted to transfer $NO^+$, $NO^-$ or $NO_2^+$ group to the helminths on being metabolized or taken up by the helminths. Anthelmintic agents substituted to transfer $NO^+$, $NO^-$ or $NO_2^+$ group to the helminths on being metabolized or taken up by the helminths include, for example, NO-substituted piperazine (e.g., as the NONOate) NO-substituted metrifonate (e.g., as the nitrite or nitrate ester), NO-substituted oxamniquine (e.g., as the nitrite or nitrate ester), NO-substituted ivermectin (e.g., as the nitrate or nitrite ester) or NO-substituted albendazole wherein the S-propyl group is replaced by S—NO. Dosage is preferably the same and route of administration is preferably the same as for the same anthelmintic agent without substitution to transfer $NO^+$, $NO^-$ or $NO_2^+$ group on being metabolized by or transported into the helminth except that in cases where NO-substitution reduces the inherent helminth inhibiting efficacy of the anthelmintic drug, the NO-substituted drug is administered in a higher dose so as to attain or exceed the original anthelmintic efficacy. The derivatizing of anthelmintic agents to release and transfer $NO^+$, $NO^-$ or $NO_2^+$ group can be carried out by standard chemical procedures. The chemical synthesis of each of the parent compounds is well-known in the literature and the processing steps necessary to achieve the modifications described are obvious to one skilled in the art. The same general procedures as described above for derivatizing antibiotics and antivirals can be used. For example, thiol group or hydroxyl group is generated if not already present and thiol or hydroxyl moieties are converted to S-nitroso thiols or nitrate or nitrite esters by well-known procedures.

We turn to the cases where the agent that selectively increases nitrosative stress is one that is administered to a mammal to inhibit proliferation (growth) of pathologically proliferating cells in the mammal.

In one case of this kind, an agent is administered which activates nitric oxide synthase in mammalian cells. Such agents include cytokines (e.g., interleukin-1, interleukin-2 and interferon-gamma), L-arginine, and calcium ionophors. Selectivity is obtained in application to inhibiting the proliferation of pathologically proliferating cancer cells by attachment to antitumor antibody (i.e., to an epitope of a cancer cell) and dosage of the antibody plus agent is 10 $\mu$g to 100 mg/kg mammalian body weight per day and the route of administration is intravenous. Selectivity is obtained in application to inhibiting the proliferation of pathologically proliferating cells that would cause restenosis by attachment of the agent to or incorporation of the agent in a polymeric stent implanted during angioplasty with the agent being present in an amount ranging from about 0.1 to 10% by weight of the polymer used in the stent and drug release being such that therapy is continued for 1 to 20 days after implantation of the stent. Selectivity is obtained in application to inhibiting the proliferation of proliferating cells causing benign prostatic hypertrophy by attachment of the agent to or incorporation of the agent in a polymeric pellet implanted in the prostate or by injection of the agent into the prostate. When used in conjunction with a pellet, the agent is present in an amount ranging from about 0.1 to 10% by weight of the polymer constituting the pellet and drug release is such that therapy is continued for 1 to 20 days after implantation of the pellet. Dosages used for injection into the prostate are 10 μg to 100 mg.

In another case of this kind, agent is administered which is a catalytic antibody that makes $NO^-$. Examples of these are those acting on anthracene-HNO cycloadduct as described in Bahr, N., et al., J. Am. Chem. Soc. 118, 3550–3555 (1996). Dosages for these are 10 μg to 100 mg/kg body weight per day, and the substrate is given at a dosage of 1 mg to 1 gm/kg body weight per day. Route of administration is local delivery to the pathologically proliferating mammalian cells. Selectivity is obtained by local delivery of the catalytic antibody.

In the case where the pathologically proliferating cells are cancer cells, a manipulator of nitrosative stress that selectively increases nitrosative stress in the pathologically proliferating cancer cells is a chemotherapeutic agent useful for treating the type of cancer involved derivatized to release and transfer $NO^+$, $NO^-$ or $NO_2^+$ group to said cells. Metabolism in the pathologically proliferating cancer cells causes release and transfer of $NO^+$, $NO^-$ or $NO_2^+$ group to the cancer cells leaving active chemotherapeutic agent. Preferred derivatives include nitrate and nitrite esters and S-nitrosothiols. Other suitable derivatives include NON-Oates (diazeniumdiolates), C-nitro and C-nitroso compounds, oxatriazoles, hydroxyguanidine compounds and other derivatives generally discussed in the chapter by M. Feelish and J. S. Stamler entitled "Donors of Nitrogen Oxides" in Methods in Nitric Oxide Research (M. Feelish and J. S. Stamler, eds.), John Wiley & Sons, Chichester, England (1991), pp 71–115, which is incorporated herein by reference. Excluded from coverage herein is the use of traditional chemotherapeutic agents which are nitrosating agents even though they have not been modified, e.g., hydroxyurea which is a hydroxyguanidine compound and is converted to nitric oxide related compound in vivo, except when they are used in combination with manipulator of nitrosative stress which is not a traditional chemotherapeutic agent. One important kind of manipulator of nitrosative stress that is chemotherapeutic agent derivatized to release and transfer $NO^+$, $NO^-$ or $NO_2^+$ group to pathologically proliferating cancer cells is alkylating agent derivatized to release and transfer $NO^+$, $NO^-$ or $NO_2^+$ group, for example, the nitrate ester of β-hydroxy melphalan, an analog of mechlorethamine in which the N-methyl group is replaced by $—CH_2CH_2ONO_2$ or $—CH_2CH_2SNO$ or $—CH_2CH_2ONO$, AZQ (diazoquone) in which the ethoxy moieties of the side chains are replaced by $—OCH_2CH_2ONO_2$ or $—OCH_2CH_2SNO$ or $—OCH_2CH_2ONO$, nitrate and nitrite esters of dianhydrogalactitol or dibromodulcitol and busulfan and hepsulfan (which contain covalently reactive alkylating moieties separated by linear alkyl chains of 4 and 7 carbon atoms respectively) where any of methylene moieties of said alkyl chains but the terminal methylene moieties are replaced with $—CHSNO—$ or $—CHONO—$ or $—CHONO_2—$; these derivatized alkylating agents are important because the alkylating moiety therein causes depletion of glutathione and thereby decreases defenses against nitrosative stress. Other manipulators of nitrosative stress that are chemotherapeutic agents derivatized to release and transfer $NO^+$, $NO^-$ or $NO_2^+$ group, include NO-substituted doxorubicin (doxorubicin causes oxidative stress which causes accumulation of glutathione disulfide at the expense of glutathione), NO-substituted daunorubicin, NO-substituted epirubicin, NO-substituted idarubucin, NO-substituted actinomycin D and NO-substituted BCNU (carmustine).

The derivatizing of a chemotherapeutic agent to release and transfer $NO^+$, $NO^-$ or $NO_2^+$ group can be carried out by standard chemical procedures. The chemical synthesis of each of the parent compounds is well-known in the literature, and the processing steps necessary to achieve the modifications described are obvious to one skilled in the art. The same general procedures as described above for derivatizing antibiotics and antivirals can be used. For example, the established syntheses for each of the agents can be altered so as to generate a thiol group at positions intended to be present as $—SNO$ or a hydroxyl group at positions intended to be occupied by $—ONO$ or $—ONO_2$ if thiol or hydroxy group is not already present. Procedures for then converting the thiol or the hydroxy moieties to S-nitroso thiols or nitrite/nitrate esters, respectively are well-known. In particular, doxorubicin, daunorubicin, epirubicin, idarubicin and actinomycin D are easily derivatized to nitrite or nitrate esters on any of the available hydroxyl moieties and all contain an amino sugar that can be derivatized with thiol acids to provide a thiol group that can be reacted with acidified sodium nitrite to form S-nitrosothiol.

In the case of the derivatized chemotherapeutic agents, the selectivity is caused by the chemotherapeutic moiety. While there is no selectivity for the chemotherapeutic moieties in terms of drug uptake, there is synergy between the activity of the original chemotherapeutic agent against rapidly dividing cells with the additional cytotoxicity of nitrosative stress that provides a selective effect. To the extent that the derivatized therapeutic agents are taken up by normal cells, the nitrosative stress so delivered is not expected to be unacceptably cytotoxic because the alkylating activity of the agent is not highly effective against non-dividing cells.

The dosage for the derivatized chemotherapeutic agents is preferably the same as the dosage employed for the same chemotherapeutic agent which is not derivatized to release and transfer $NO^+$, $NO^-$ or $NO_2^+$ group, except that in cases where NO-substitution reduces the inherent chemotherapeutic efficacy of the drug, the NO-substituted drug is administered at higher dose so as to attain or exceed the original chemotherapeutic efficacy. The route of administration for the derivatized chemotherapeutic agents is the same as that employed for the same chemotherapeutic agent which is not derivatized. For example, the recommended dosage for melphalan ranges from 0.1 to 2.5 mg/kg and the preferred route of administration is oral or intravenous and the same dosage range and route of administration can be employed in the invention herein for melphalan derivatized to release and transfer $NO^+$, $NO^-$ or $NO_2^+$ group.

Another kind of manipulator of nitrosative stress that selectively increases nitrosative stress in pathologically proliferating cancer cells is nitrosating agent, preferably S-nitrosothiol, employed with chemotherapeutic agent (which functions by a mechanism other than by manipulating nitrosative stress). Selectivity is caused by the chemotherapeutic agent. While there is no selectivity for the nitrosating agent in terms of drug uptake, there is selectivity of effect between the activity of the chemotherapeutic agent and the nitrosating agent with the nitrosating agent providing additional cytotoxic effect in respect to the proliferating cells. Examples of S-nitrosothiols are the same as those listed above in respect to treating helminth infections. The dosage for the nitrosating agent ranges from 1 mg to 10 gm/kg body weight per day with oral administration being preferred with other routes of administration including parenteral (e.g., intravenous) also being useful. The chemotherapeutic agents are used in the same dosages and with the same routes of administration as are employed when they are used without nitrosating agents.

Another kind of manipulator of nitrosative stress that selectively increases nitrosative stress in pathologically proliferating cancer cells is antitumor antibody (i.e., to an epitope on a cancer cell) to which has been attached nitrosative stress agent such as S-nitrosothiol. For example, reaction of the antitumor antibody with methyl 3-(S-nitroso) propionimidate derivatives solvent exposed amino groups of lysine side chains to form stable amidine linkages with the S-nitrosothiol (i.e., $ONSCH_2CH_2C(=NH_2^+)$—NH-Lys). Dosage for this agent ranges from 0.1 mg to 100 mg/kg body weight per day and route of administration is intravenous.

In a preferred method applicable to mammals afflicted with pathologically proliferating cancer cells, two kinds of manipulators of nitrosative stress are administered, and one kind is an inhibitor of protection against nitrosative stress and the other kind is an agent that increases nitrosative stress and one or both of the two kinds of manipulators of nitrosative stress is(are) selective for effect in the cancer cells. A manipulator of nitrosative stress that may be administered in this embodiment to inhibit protection against nitrosative stress which is not selective for this purpose in pathologically proliferating cancer cells is, for example, L-buthionine-S-sulfoximine (for which the dosage ranges from 1 to 50 mmol per kg mammal body weight per day and the route of administration is preferably intravenous). Examples of manipulators of nitrosative stress that may be administered in this embodiment to selectively inhibit protection against nitrosative stress in pathologically proliferating cancer cells are the same manipulators of nitrosative stress described to have this function hereinbefore, e.g., antitumor antibody cross-linked by ester linkage to L-buthionine-S-sulfoximine, and the dosages and routes of administration are the same as those discussed hereinbefore. Manipulators of nitrosative stress that may be used in this embodiment to selectively increase nitrosative stress in pathologically proliferating cancer cells are the chemotherapeutic agents derivatived to release and transfer $NO^+$, $NO^-$ or $NO_2^+$ group described above, and the dosages and routes of administration described above in conjunction with these agents may be used for these agents in this embodiment, or are antitumor antibodies to which have been attached nitrosative stress agents as described above utilized with the dosages and routes of administration described above in connection with them. Manipulators of nitrosative stress that may be used in this embodiment to increase nitrosative stress in pathologically proliferating cancer cells which are not selective for this purpose are, for example, S-nitrosocysteine, nitroglycerine, and amyl nitrite, and the dosages and routes of administration associated with each of these are respectively 10 mg to 1 gm (oral or intravenous), 1 to 5 mg (orally) or 5 µg/min (intravenous) and 0.1 to 0.3 ml (inhaled).

In the case where the pathologically proliferating cells are proliferating cells that would cause restenosis, the manipulator(s) of nitrosative stress that is (are) administered to inhibit the proliferation of the pathologically proliferating cells is (are) (i) manipulator of nitrosative stress that inhibits protection against nitrosative stress or (ii) manipulator of nitrosative stress that is agent that increases nitrosative stress employed concurrently with a manipulator of nitrosative stress that inhibits protection against nitrosative stress or (iii) manipulator of nitrosative stress that both increases nitrosative stress and inhibits protection against nitrosative stress. Selectivity is obtained by associating the one manipulator of nitrosative stress that is employed or at least one of a plurality of manipulators of nitrosative stress that are employed with a stent implanted during angioplasty. For example, manipulator(s) of nitrosative stress is (are) attached to a polymeric stent via an ester linkage to polymer of the stent or is (are) associated with a porous polymer coated on a stent whereby manipulator(s) of nitrosative stress leach(es) out of the porous polymer and contact(s) the pathologically proliferating cells. The manipulator(s) of nitrosative stress used in association with a polymeric stent or with polymer coated on a stent is (are) employed in an amount ranging from 0.1 to 10% by weight of the polymer. Suitable manipulators of nitrosative stress that inhibit protection against nitrosative stress for (i) include, for example, agents which inhibit the synthesis of glutathione or deplete glutathione non-selectively when not locally delivered, e.g., L-buthionine-S-sulfoximine, diethyl maleate or melphalan. Suitable manipulators of nitrosative stress that increase nitrosative stress for (ii) include, for example, S-nitrosocysteine, nitroglycerine, amyl nitrite and S-nitrosopolythiodextran. Suitable manipulators of nitrosative stress that inhibit protection against nitrosative stress for (ii) include, for example, melphalan, and thiol synthesis inhibiting agents, e.g., L-buthionine-S-sulfoximine. In one alternative for (ii), both kinds of manipulators of nitrosative stress are administered from a stent. In other alternatives for (ii), L-buthionine-S-sulfoximine is administered from a stent and agent that increases nitrosative stress is administered systemically, e.g., intravenously, or by intracoronary infusion or agent that increases nitrosative stress is administered from a stent or by intracoronary infusion and L-buthionine-S-sulfoximine is administered systemically. Where L-buthionine-S-sulfoximine is administered systemically, it is preferably used in a dosage ranging from 1 mmol to 100 mmol per kg mammalian body weight per day and administration is preferably by oral administration. Where agent that increases nitrosative stress (e.g., S-nitrosocysteine or S-nitrosopolythiodextran) is administered systemically, it is preferably used in a dosage ranging from 0.1 µg to 100 mg per kg mammalian body weight per day and administration is preferably by oral or intravenous administration. Suitable manipulator of nitrosative stress for (iii) is NO-substituted L-buthionine-S-sulfoximine, preferably administered from a stent where it is present in an amount ranging from 0.1 to 10% by weight of the polymer of the stent and the rate of drug release is such that therapy continues for 1 to 20 days or longer. The treatments are optionally used in combination with intravascular beta-, gamma- or X-ray irradiation. Methods for applying beta- and gamma-irradiation for this purpose are described hereinbefore.

In cases where the pathologically proliferating cells are the cells causing benign prostatic hypertrophy, selectivity can be obtained by associating the manipulator(s) of nitrosative stress with an implant which is inserted into the affected prostate. The manipulator of nitrosative stress can be one that increases nitrosative stress or the manipulator of nitrosative stress can be one that inhibits protection against nitrosative stress, e.g., L-buthionine-S-sulfoximine. Preferably, the two types of manipulators of nitrosative stress are used together. Where two kinds of manipulators of nitrosative stress are utilized, only one kind need be selective, so only one kind may be attached to the implant and the other kind may be non-selective and administered systemically or both kinds can be administered from the implant. The implant is preferably a polymer pellet as described hereinbefore and the associated agent is present in an amount ranging from 0.1 to 10% by weight of the polymer in the pellet and rate of drug release is such that therapy continues for 1 to 20 days or longer after the pellet is emplaced. Selective application can also be obtained by systemic administration of glutathione synthesis inhibiting agent or glutathione depleting agent, in dosages ranging from 1 mmol/kg to 100 mmol/kg of mammalian body weight per day and/or nitrosating agent in dosages ranging from 1 mg to 1 g/kg body weight per day, with co-administration of drug that does not manipulate nitrosative stress that inhibits benign prostatic hypertrophy, e.g., phenoxybenzamine, alfuzosin, prazosin, tetrazosin, doxazosin, tamsulosin and finasteride in the dosages and with the routes of administration used for this purpose. Selective application can also be obtained by systemic administration of NO-substituted drug that otherwise does not manipulate nitrosative stress that inhibits benign prostatic hypertrophy. The same general procedures as described above for derivatizing antibiotics and antivirals can be used to obtain the NO-substitution. For example, thiol group or hydroxyl group is generated if not already present, and thiol or hydroxyl moieties are converted to S-nitrosothiols or nitrate or nitrite esters by well-known procedures. An examples of an NO-substituted benign prostatic hypertrophy drug is NO-substituted finasteride (e.g., as the NONOate). Dosage is preferably the same as for the same benign prostatic hypertrophy drug except that in cases where the NO-substitution reduces the inherent efficacy of the benign prostatic hypertrophy drug, the NO-substituted drug is administered in a higher dose so as to attain or exceed the original benign prostatic hypertrophy ameliorating efficacy. The route of administration for the NO-substituted drug is preferably the same as for the same drug without NO-substitution.

In all the cases described above except where otherwise specifically stated, two kinds of manipulators of nitrosative stress in the pathologic microbes or in the host cells infected with said microbes or in the pathologic helminths or in the pathologically proliferating mammalian cells can be employed where one kind is an inhibitor of protection against nitrosative stress and the other kind is an agent that increases nitrosative stress in the microbes, host cells, helminths or pathologically proliferating mammalian cells, and either the inhibition of protection against nitrosative stress or the increasing of nitrosative stress or both are selective in said microbes, host cells, helminths and proliferating mammalian cells. Examples of selective agents are described hereinbefore. Examples of the non-selective agents are L-buthionine-S-sulfoximine and ethacrynic acid (a thiol depleter) administered systemically, e.g., via oral or intravenous routes of administration, at a dosage of 0.1 µg to 100 mg/kg body weight per day. In a preferred execution, a single agent is used which is both an inhibitor of protection against nitrosative stress and an increaser of nitrosative stress in the pathologic microbes or in host cells infected with pathologic microbes or in the pathologic helminths or in the pathologically proliferating mammalian cells.

Another embodiment herein is directed to treating microbial infections of the oral cavity in a mammal comprising topically administering to the site of the infection an infection reducing effective amount of a manipulator of nitrosative stress which increases nitrosative stress in microbes causing the microbial infection, especially S-nitrosothiols. This method is important especially for immunocompromised patients, e.g., for treating oral candidiasis. Examples of S-nitrosothiols for this embodiment include S-nitrosoglutathione, S-nitroso-N-acetylpenicillamine, S-nitroso-gamma-methyl-L-homocysteine, S-nitroso-L-homocysteine and S-nitroso-δ-thio-L-leucine. The S-nitrosothiols are utilized at concentrations ranging from 0.1 mM to 1 M, e.g., in solution in water or saline and are preferably applied as an oral rinse. For example, a suitable treatment regimen is for the patient to orally swish 5 ml of a 100 mM S-nitrosothiol solution for a 1 to 5 minute time period and then to spit it out, four times a day, for as long as improvement is obtained.

Another embodiment herein is directed to infected skin lesions (microbe-caused infection) in a mammal comprising topically administering to the skin lesions an infection reducing effective amount of an S-nitrosothiol. The skin lesions to which this method applies include, for example, those of athlete's foot fungal infections, herpetic lesions, and infected skin ulcers. The S-nitrosothiols can be those described in the above paragraph used at concentrations ranging from 0.1 mM to 1 M. The S-nitrosothiols can also be formed in situ, e.g., by applying a mixture of inorganic nitrite salt (e.g., sodium nitrite), pharmaceutically acceptable acid (e.g., salicylic acid or citric acid), and thiol (e.g., cysteine), in proportions suitable for forming an S-nitrosothiol. For this method, the S-nitrosothiol or mixture for forming an S-nitrosothiol is readily formulated into a composition for topical application, for example, an ointment or cream, by admixture with inactive ingredients that are conventional for compositions for topical application. The compositions can be applied, for example, one to four times a day, for as long as benefit is obtained.

Another embodiment herein is directed to treating protozoal infections in a mammal and comprises systemically administering to said mammal an infection reducing amount of L-buthionine-S-sulfoximine and of agent that increases nitrosative stress. Examples of pathologic conditions associated with protozoa that can be treated in this embodiment are those listed hereinbefore. The dosage for the L-buthionine-S-sulfoximine is 1 to 50 mmol per kg mammal body weight per day and route of administration is preferably oral. The agent that increases nitrosative stress is nitrate or nitrite ester or nitrosothiol. Examples of S-nitrosothiols include S-nitrosoglutathione, S-nitroso-N-acetylpenicillamine, S-nitrosocysteine, N-nitroso-gamma-methyl-L-homocysteine, S-nitroso-L-homocysteine, S-nitroso-gamma-thio-L-leucine, and S-nitroso-δ-thio-L-leucine. The dosage for the agent that increases nitrosative stress is 1 µg to 10 gm/kg and often 10 µg to 1 g/kg or 100 µg to 100 mg/kg body weight per day.

NO-substituted drugs and NO-substitution are referred to herein. The terms "NO-substituted" and "NO-substitution" are used herein to describe drugs derivatized to be nitric oxide related compounds as defined above or to release nitric oxide in an environment where some of the nitric oxide is converted to nitric oxide related compounds. NO-substituted drugs include drugs in which pre-existing hydroxyl groups are modified to nitrite or nitrate esters, pre-existing sulfhydryl groups are modified to S-nitrosothiols, or pre-existing secondary amino groups are modified to NONOates. They also include drugs in which pre-existing amino or hydroxyl groups are amidated or esterified, respectively, with carboxylic acids bearing hydroxyl, thiol, or secondary amino groups that are in turn derivatized as nitrite or nitrate esters, S-nitrosothiols, or NONOates respectively. They also include drugs in which pre-existing carboxylic acid groups are converted to amides or esters in which the amine or alcohol attached to the carboxylates also bears hydroxyl, thiol, or secondary amino groups which are in turn converted to nitrite or nitrate esters, S-nitrosothiols, or NONOates, respectively. The NO-substituted drug should maintain at least 10% of its original therapeutic activity or should be converted at its site of action to a species with at least 10% of its original activity (e.g., through loss of nitrite or nitrate ester functionality, transfer of $NO^+$ from S-nitrosothiol, decomposition of NONOate, or enzymatic or non-enzymatic hydrolysis of carboxylate substituents or pre-existing amino or hydroxyl group substituents).

Another embodiment herein is directed to inhibiting growth of pathologic microbes or pathologic helminths or pathologically proliferating mammalian cells, in a mammal, said method comprising administering to said mammal a pathologic microbe or pathologic helminth or pathologically proliferating mammalian cell anti-proliferative effective amount (dosage) of a manipulator of nitrosative stress in said microbes or in host cells infected with said microbes or in said helminths or in said pathologically proliferating mammalian cells and an agent which increases oxidative stress in said microbes or host cells or helminths or pathologically proliferating mammalian cells whereby the combination of manipulator and agent selectively kills or reduces the growth of said microbes or helminths or mammalian cells or enhances their susceptibility to innate immune defenses or the susceptibility of the microbes to antimicrobial agents (which function by a mechanism different from increasing oxidative stress or manipulating nitrosative stress) or the susceptibility of the helminths to anthelmintic agents (which function by a mechanism different from increasing oxidative stress or manipulating nitrosative stress) or the susceptibility of the pathologically proliferating mammalian cells to antiproliferation agents (which function by a mechanism different from increasing oxidative stress or manipulating nitrosative stress). The pathologic microbes, pathologic helminths, and pathologically proliferating mammalian cells are those described above. The manipulators of nitrosative stress are those described above in conjunction with other embodiments and these may be used with the dosages and routes of administration described above. The agents which increase oxidative stress in said microbes, host cells, helminths, and pathologically proliferating mammalian cells can be, for example, redox cycling drugs (e.g., doxorubicin), organic peroxides, immune system stimulants causing a respiratory burst and 100% oxygen administered in a hyperbaric chamber and the dosages and routes of administration used for these are those established for the use of these agents for other purposes. The same agent can be used as a manipulator of nitrosative stress and to increase oxidative stress. An example of this in the treatment of a human patient with pathologically proliferating cancer cells is doxorubicin derivatized to release and transfer $NO^+$, $NO^-$ or $NO_2^+$ group described above, used with dosages and routes of administration described above.

The function of administration of manipulators and/or agents herein to enhance the susceptibility of microbes and helminths and pathologically proliferating mammalian cells to innate immune defenses is recited herein. It is now appreciated that cells of the immune system (e.g., macrophages, neutrophils, etc.) employ a variety of mechanisms to kill. microbes or helminths or pathologically proliferating mammalian cells. In some cases the pathologic cell, typically a microbe, is phagocytized by the cell of the immune system and is attacked inside a vesicle within the immune cell, and in other cases the immune cell attacks the pathologic cell without first phagocytizing it. In either case, two important components of the immune cell cytostatic or cytotoxic response to the pathologic cell are the production of oxidative stress agents (e.g., superoxide, hydrogen peroxide, hypochlorous acid, peroxynitrite) and nitrosative stress agents (e.g., S-nitrosothiols, $N_2O_3$, etc.). Pathologic microbes and pathologic helminths and pathologically proliferating mammalian cells have defenses against both oxidative and nitrosative stress and among these defenses are endogenous thiols which reduce oxidative stress agents or react with nitrosative stress agents to form less cytotoxic species, export pumps in the plasma membrane which remove, for example, S-nitrosoglutathione from the cells thereby reducing the potential toxicity of that species to the cells, and various enzymes which degrade oxidative stress agents (e.g., superoxide dismutase, catalase, glutathione peroxidase, etc.) or nitrosative stress agents (e.g., the thioredoxin system degrades S-nitrosoglutathione, etc.). Consequently, thiol depletion or inhibition of these enzymes increases the susceptibility of pathologic microbes or pathologic helminths or pathologically proliferating mammalian cells to oxidative and nitrosative stress provided by the immune system of the host organism.

The function of administration of manipulators and/or agents herein to enhance the susceptibility of microbes to antimicrobial agents is mentioned herein. This is important because certain strains of bacteria have developed which are resistant to antimicrobial agents, e.g., drug resistant staphylococci, streptococci, *E. coli* and *Mycobacterium tuberculosis*. The invention herein can make these antimicrobial resistant bacteria susceptible to antimicrobial agents including antibiotics.

Another embodiment herein is directed to a method for inhibiting growth of pathologic bacteria in a mammal, said method comprising administering to said mammal a pathologic bacteria antiproliferative effective amount of a chelating agent and of an agent that increases nitrosative stress. Metal ions, principally copper and iron, catalyze the breakdown of S-nitrosothiols, a major category of nitrosative stress agents, in vivo. Agents chelating copper or iron decrease the ability of microorganisms to destroy S-nitrosothiols and thereby avoid the toxicity of S-nitrosothiols. Suitable chelating agents for use in this embodiment are those that bind copper and/or iron and include, for example, penicillamine (a copper chelator) administered orally in a dose ranging from 0.1 to 2.5 g/day in four divided doses; trientine (a copper chelator) administered orally in a dose ranging from 0.5 to 2 g/day in divided doses two, three or four times daily; and deferoxamine (an iron chelator) administered subcutaneously in a dose ranging from 0.1 to 2 g/day. The agents in this embodiment that increase nitrosative stress include the manipulators of nitrosative stress for selectively increasing nitrosative stress in microbes described above, and routes of administration described above for these apply in this embodiment. The agent that increases nitrosative stress in this embodiment can also be one that by itself is non-selective since the combination of manipulator of nitrosative stress and chelating agent provides selective application since microbes are more sensitive to this combination than normal mammalian cells. Non-selective agents for increasing nitrosative stress and dosages and routes of administration for systemic delivery are described above. The bacteria to which this embodiment applies include those listed above.

Still another embodiment herein is directed at a method of inhibiting growth of pathologic microbes or pathologic helminths or pathologically proliferating mammalian cells, in a mammal, said method comprising administering to said mammal a therapeutic pathologic microbe or pathologic helminth or pathologically proliferating mammalian cell antiproliferative effective amount of a manipulator of nitrosative stress comprising agent functional to convert endogenously produced NO to $NO^-$ or $NO^+$ (including species with $NO^+$ activity which are nitric-oxide related compounds). The pathologic microbes, pathologic helminths and pathologically proliferating mammalian cells are those described above. Example of agent that is functional to convert endogenously produced NO to $NO^-$ or $NO^+$ is redox active metal catalyst, especially chelates of iron which are known to be redox active metal catalysts. An example of a redox active metal catalyst that is functional to convert endogenously produced NO to $NO^-$ is ferrioxamine B complex which is referred to as [Fe(III)(HDFB)]+ and as a stable and efficient electrocatalyst for the reduction of NO to $NO_2$ at biologically relevant potentials in Kazmierski, W. M., et al., Proc. Natl. Acad. Sci. USA, Vol. 93, pp 9138–9141 (8/1996). The disclosure of Kazmierski, et al., is incorporated herein by reference. Redox active metal catalysts functional to convert NO to $NO^+$ are described in Stamler, J., et al., Science, Vol. 258, 1898–1902 (1992), the disclosure of which is incorporated herein by reference. Redox active catalysts functional to convert NO to species with $NO^+$ activity are heme complexes including myoglobin and hemoglobin. The redox active metal catalysis are used with dosages of 10 µg to 100 mg/kg body weight per day and administration is preferably via oral or intravenous routes. Preferably cytokines are also administered which induce iNOS to cause increase of endogenous NO production resulting in higher levels of nitrosative stress because of greater efficiency of conversion to nitrosative stress species because of the greater amount of NO being produced. Cytokines useful in this embodiment to induce iNOS to cause increased endogenous NO production include interleukin-1, interleukin-2 and tumor necrosis factor. Dosages for the cytokines are 1 µg to 10 mg/kg body weight per day for 1 to 10 days and route of administration is intravenous.

Still another embodiment herein is directed to a method for inhibiting growth of pathologically proliferating mammalian cells or for killing or inhibiting growth of mammalian host cells containing pathologic microbes (i.e., mammalian cells with viruses or microbes that are living inside the mammalian cells), in a mammal, comprising administering to said mammal a pathologic microbe or a pathologically proliferating mammalian cell antiproliferative effective amount of a blocker of the ability of the cells to export nitrosant and an agent that increases nitrosative stress. In explanation, mammalian cells defend themselves against nitrosants using their endogenous glutathione. Nitrosant reacts with glutathione to form S-nitrosoglutathione and therefore is not available to nitrosate more critical structures such as proteins or nucleic acids. S-Nitrosoglutathione itself might cause some toxicity, but cells have developed export pumps which they use to transport S-nitrosoglutathione (as well as other S-substituted glutathiones) out of the cell into the extracellular environment. Once such agents are outside the cell, they are carried away with the extracellular fluid and are much less likely to damage the cell from which they were exported. To summarize, a highly reactive nitrosant such as $N_2O_3$ or S-nitrosocysteine can react with glutathione to form S-nitrosoglutathione which is itself less reactive than the original species and which in addition is subject to selective export from the cell eliminating its toxicity to the cell. Blocking the export, as is the case in this embodiment, keeps the S-nitrosoglutathione and other nitrosated products in the cell where their toxicity is applied to the cell. Increasing nitrosative stress in the cell causes an increased amount of nitrosated products in the cell where their toxicity is applied to the cell. We turn now to the pathologic microbes; these are the same as those described above. We turn now to the pathologically proliferating mammalian cells; these are the same as the pathologically proliferating cells described above, and include, for example, pathologically proliferating cancer cells, the pathologically proliferating or enlarging cells that would cause restenosis and the pathologically proliferating or enlarging cells causing benign prostatic hypertrophy. We turn now to the blockers of the ability of the cells to export nitrosant. The blocker is preferably a substrate for P-glycoprotein or an inhibitor of P-glycoprotein. Inhibitors of P-glycoprotein include, for example, verapamil, cyclosporin, S9788, MK571 and stable S-substituted derivatives of glutathione, e.g., the 2,4-dinitrophenyl derivatives of glutathione (e.g., dinitrophenacyl glutathione). Other blockers are derivatives of glutathione in which the thiol moiety of glutathione is covalently substituted with alkyl, aryl or aralkyl where the glycyl carboxylate or both the glycyl and α-glutamyl carboxylate are esterified (e.g., with ethanol). Preferably the blocker is administered locally or is otherwise administered so as to be selective for the host cells or for the pathologically proliferating mammalian cells. The antiproliferative effective amount (dosage) of the blocker may range from 0.1 µg to 100 mg per kg of mammal body weight and the route of administration for it is topical or intravenous or oral. The agents in this embodiment that increase nitrosative stress can be the same as the manipulators of nitrosative stress administered to selectively increase nitrosative stress described above and the dosages and routes of administration described above for these apply in this embodiment. The agent that increases nitrosative stress in this embodiment can also be one that, on administration, is non-selective for host cells and pathologically proliferating mammalian cells, for example, NO-substituted verapamil (produced, for example, by replacing the methyl group in the isopropyl moiety of verpamil with —SNO or by removing the N-methyl group of verapamil and using the resulting dialkylamine as the basis for forming a NONOate which will release NO for partial conversion to nitrosant) or S-nitroso-N-acetylpencillamine administered intravenously or nitroglycerin administered orally, in a dosage of 10 µg to 100 mg/kg mammalian body weight per day. In the case of NO-substituted verpamil, a single agent functions as a blocker of the ability of the cells to export nitrosant and as agent which increases nitrosative stress.

In those embodiments herein where a manipulator of nitrosative stress that is nitrosant or NONOate is administered systemically, a hypotensive response can occur. Sometimes there is an adaptive response where the agent continues to cause nitrosative stress but not cause hypotension after 24–48 hours, e.g., in the case where organic nitrates are administered. The hypotension occurs because nitric oxide activates the soluble isoform of guanylyl cyclase which forms cyclic GMP (cGMP) which causes alterations in cellular calcium levels that eventually cause smooth muscle relaxation and hypotension. In those cases where a hypotensive response occurs, especially where there will be no adaptive response, the hypotensive response is prevented by administration of an inhibitor of guanylyl cyclase, e.g., methylene blue, LY83583 which is 6-anilino-5,8-quinolinedione, or OQD which is 1H-[1,2,4]oxadiazole[4,3-a]quinoxalin-1-one. Thus, an embodiment herein is directed to a method of inhibiting growth of pathologic microbes or pathologic helminths or pathologically proliferating mammalian cells, in a mammal, comprising systemically administering to said mammal a pathologic microbe or pathologic helminth or pathologically proliferating mammalian cell antiproliferative effective amount of agent that increases nitrosative stress in said microbes or in host cells infected with said microbes or in said helminths or in said pathologically proliferating cells whereby nitrosative stress selectively kills or reduces the growth of said microbes or host cells or helminths or pathologically proliferating mammalian cells or selectively enhances their susceptibility to innate immune defenses or the susceptibility of said microbes to antimicrobial agents (which function by a mechanism other than by manipulating nitrosative stress) or the susceptibility of said helminths to anthelmintic agents (which function by a mechanism other than by manipulating nitrosative stress) or the susceptibility of the pathologically proliferating cells to antiproliferative agents (which function by a mechanism other than by manipulating nitrosative stress), and also administering to said mammal a hypotensive response preventing amount of an inhibitor of guanylyl cyclase, e.g., at a dosage ranging from 10 µg to 100 mg/kg body weight via intravenous or oral route of administration.

We turn now to the method herein of inhibiting growth of non-viral pathologic microbes in a mammal, said method comprising administering to said mammal a pathologic microbe antiproliferative effective amount of a selective inhibitor of thiol synthesis in the microbe to mediate selective killing or growth reduction of the microbe by agent which is selected from the group consisting of antimicrobials, immune cells in the mammal and products of mammalian antimicrobial response. The selective inhibitors of thiol synthesis are the same as those described above as manipulators of nitrosative stress which are selective inhibitors of thiol synthesis in microbes and the antiproliferative effective amounts for this embodiment are the same as the dosages described above for manipulators of nitrosative stress which are selective inhibitors of thiol synthesis in microbes and the routes of administration are the same as those described above in conjunction with manipulators of nitrosative stress which are selective inhibitors of thiol synthesis in microbes. Where the microbes are glutathione-producing microbes, the selective inhibitors of thiol synthesis are preferably α-alkyl-S-alkyl-homocysteine sulfoximines, e.g., α-alkyl-S-alkyl-DL-homocysteine-RS-sulfoximines or the L,S-diastereomers, where the α-alkyl contains 2 to 8 carbon atoms and the S-alkyl contains 1 to 10 carbon atoms, very preferably where the α-alkyl is ethyl and/or the S-alkyl is butyl, e.g., α-ethyl-L-buthionine-S-sulfoximine, with the dosages and routes of administration described above for these applying here. The antimicrobials are those having antimicrobial effect on the infecting microbe and include, for example, chloramphenicol for the treatment of *E. coli* caused septicemia and isoniazid and rifampin for the treatment of *Mycobacterium tuberculosis* caused tuberculosis. The immune cells in the mammal include, for example, macrophages and neutrophils. The products of mammalian antimicrobial response include, for example, S-nitrosothiols and $N_2O_3$ and oxidative stress agents, for example, hydrogen peroxide, superoxide and hypochlorous acid.

We turn now to the method herein for inhibiting the growth of pathologic viruses in a mammal (including a human), said method comprising administering to the mammal a therapeutic amount of a non-selective inhibitor of glutathione synthesis or depleter of glutathione which causes depletion of glutathione in the host cells for the virus and thereby sensitizes the virus to selective killing by antiviral agent, immune cells in the mammal and products of the mammalian antiviral response. Viral infections treated by this method include, for example, those mentioned hereinfore in reference to pathologic viruses and include, for example, infections caused by human immunodeficiency virus (AIDS, Kaposi's sarcoma), herpes virus (herpetic infections), cytomegalovirus (pneumonia, CMV mononucleosis), Epstein Barr virus (infectious mononucleosis, Burkitt's lymphoma), hepatitis viruses A, B and C (hepatitis), and rotavirus (viral gastroenteritis). In its broadest aspect, this method comprises administering to the mammal a non-selective inhibitor of glutathione synthesis or depleter of glutathione which depletes glutathione in the host cells for the virus. Examples of non-selective inhibitors of glutathione synthesis and depleters of glutathione are L-buthionine-S-sulfoximine, ethacrynic acid, L-prothionine-S-sulfoximine, L-penthathionine-S-sulfoximine, and diethyl maleate; these are administered systemically, e.g., via oral or intravenous routes of administration, at a dosage of 0.1 µg to 100 mg/kg body weight per day. The non-selective inhibitors of glutathione synthesis or depleters of glutathione are preferably administered in conjunction with antiviral agent. The antiviral agents are those used for the viral infection being treated used in those doses and with the routes of administration for the antiviral agent and include zidovudine, acyclovir, penciclovir, famciclovir, interferon-α, interferon-β, and interferon-gamma.

We turn now to the method herein comprising treating a mammal, e.g., a human, for those disorders now being treated with hydroxyurea with a therapeutic amount of a non-selective inhibitor of glutathione synthesis or depleter of glutathione used in conjunction with the hydroxyurea. The disorders now being treated with hydroxyurea include myeloproliferative disorders (including chronic granulocytic leukemia, polycythemia vera, and essential thrombocytosis), malignant melanoma, and carcinomas of the head, neck and genitourinary systems, and psoriasis. The inhibitor of glutathione synthesis or depleter of glutathione is administered to decrease defenses against nitrosative stress. The hydroxyurea is converted to nitric-oxide related compounds in vivo and therefore causes nitrosative stress. Examples of inhibitors of glutathione synthesis and depleters of glutathione for this embodiment are L-buthionine-S-sulfoximine, ethacrynic acid, L-prothionine-s-sulfoximine, L-pentathionine-S-sulfoximine, and diethyl maleate; these are administered systemically, e.g., via oral or intravenous routes, in a therapeutic amount, e.g., at a dosage of 0.1 µg to 100 mg/kg body weight per day. The hydroxyurea is administered in the dosages and with the routes of administration used for the disorder being treated. In general, the dosage for hydroxyurea normally ranges from 20 to 80 mg/kg body weight, e.g., 80 mg/kg administered orally as a single dose every third day or 20–30 mg/kg administered orally as a single daily dose.

We turn now to the novel α-alkyl-S-alkyl-homocysteine sulfoximines where the α-alkyl contains 2 to 8 carbon atoms and the S-alkyl contains 1 to 10 carbon atoms (especially the corresponding DL,RS compounds and the L,S-diastercomers), which constitute another embodiment herein. The method of making these is described above.

α-Ethyl-D,L-buthionine-R,S-sulfoximine is an example of a species of the genus. It has the structure set forth below:

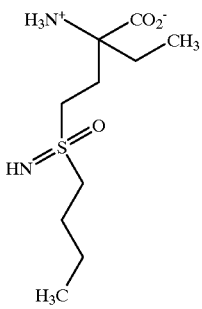

It has a melting point of 203–205 degrees C. Proton, $^{13}$C NMR and elemental analysis data obtained on the synthesized compound is set forth hereinafter: $^1$H-NMR (D$_2$O): δ 0.93–0.98 [tt, 6H, —C(NH$_2$)(COOH)CH$_2$CH$_3$S(=O)(=NH)CH$_2$CH$_2$CH$_2$CH$_3$], 1.42 [q, 2H, —S(=O)(=NH)CH$_2$CH$_2$CH$_2$CH$_3$], 1.7–2.1 [m, 4H, C(NH$_2$)(COOH)CH$_2$CH$_3$S(=O)(=NH)CH$_2$CH$_2$CH$_2$CH$_3$], 2.29 [q, 2H, —C(NH$_2$)(COOH)CH$_2$CH$_2$S(=O)(=NH)] and 3.1–3.39 [tt, 4H, —C(NH$_2$)(COOH)—CH$_2$CH$_2$S(=O)(=NH)CH$_2$CH$_2$CH$_2$CH$_3$]. $^{13}$C-NMR (D$_2$O): δ 9.93, 15.40, 23.60, 26.30, 31.25, 31.83, 51.83, 55.84, 66.77 and 176.91. Elemental analysis: Calculated for C$_{10}$H$_{22}$N$_2$O$_3$S,0.5H$_2$O, C, 46.33; H, 8.88; N, 10.81. Observed, C, 46.95; H, 8.82; N, 11.17.

We turn now to the invention herein related to treating patients in need of increased nitrosative stress defenses.

One kind of patient in need of increased nitrosative stress defenses, is a patient who has had a transient ischemic attack. Transient ischemic attacks are defined in *The Merck Manual*, 16th edition, as "Focal neurologic abnormalities of sudden onset and brief duration (usually minutes, never more than a few hours) that reflect dysfunction in the distribution of either the internal carotid-middle cerebral or the vertebral-vascular arterial system." In some patients, transient ischemic attacks occur shortly before a stroke. In other patients who have had one or more transient ischemic attacks, stroke eventually occurs; this scenario is more prevalent in those patients with carotid artery involvement. There is now evidence that nitrosative stress can contribute importantly to the tissue damage and disability of cerebral stroke.

One embodiment herein is directed to prophylactically treating those patients who have had one or more transient ischemic attacks or a prior stroke so as to protect neuronal cells from death in the event a stroke later occurs in such a patient. This embodiment is directed to a method of treating a patient at risk for a cerebral stroke because of having had one or more transient ischemic attacks or a prior stroke, said method comprising administering to said patient a nitrosative stress defense mechanism upregulating amount of manipulator of nitrosative stress in the patient thereby to cause protection of neuronal cells in the patient from death from nitrosative stress occurring in the patient in the event a cerebral stroke occurs in the patient.

A method for causing upregulation of nitrosative stress defense mechanism in patients needing such including those who have had one or more transient ischemic attacks or a prior stroke comprises the administration to such a patient of a nitrosative stress tolerance increasing amount of a manipulator of nitrosative stress. Thus, an embodiment herein is directed to a method of treating a patient in need of increased nitrosative stress defenses, e.g., a patient who is at risk for a stroke because of having had one or more transient ischemic attacks or who has had one or more strokes and is therefore at risk for another stroke, and comprises administering to said patient a nitrosative stress tolerance increasing amount of a manipulator of nitrosative stress thereby to cause increase of nitrosative stress defense mechanism in the patient. The manipulator of nitrosative stress for this embodiment can be one that imposes a nitrosative stress or one that is metabolized in the body to one that imposes nitrosative stress or agent that is one that inhibits protection against nitrosative stress, which is administered repeatedly, usually at low doses, to cause an increase in tolerance to nitrosative stress, i.e., to cause a tolerance enhancing response of upregulating nitrosative defense mechanism, in the patient. The method herein can be effected for example, by administering, preferably nasally, low concentrations (e.g., 1 to 10 ppm in air) of nitrogen dioxide (NO$_2$), dinitrogen trioxide (N$_2$O$_3$) or dinitrogen tetroxide (N$_2$O$_4$) for 0.1 to 4 hours for 1 to 30 days or at concentrations of 1 to 2 ppm for 0.1 to 1 hour indefinitely. Other specific methods of upregulating nitrosative stress defense mechanism in a patient include administering nitroglycerin, e.g., orally, at a dose ranging from 3 to 13 mg, four times a day, for three days to three weeks, or via sublingual administration at a dose ranging from 0.15 to 0.6 mg up to 10 times per day or at least 50 times a week, for one week; administering S-nitrosocysteine, intravenously, intranasally or orally, at a dose of 0.1 mg to 10 mg, six times per day for three days to three weeks; administering a redox cycling drug; i.e., a drug which is reduced by enzymes using NADPH or NADH, to a species that reacts spontaneously with O$_2$ to give superoxide, e.g., doxorubicin or menadione, at a dosage which is 1 to 100% of that used for the drug for its known therapeutic usage, daily, for up to four days via the route of administration used for the drug; administering hyperbaric oxygen, i.e., 100% O$_2$ (containing up to 100 ppm NO) at 1 to 3 atmospheres, two or three times per day for 30 minutes, repeating for up to 10 days; administering amyloid peptide, e.g., amino acids 1–40 of amyloid protein or any of those described in established literature, at doses of 1 μg to 100, daily, or at least three times a week, for at least two weeks, via intravenous route of administration; or administering L-buthionine-S-sulfoximine (LBSO) or its ethyl ester, preferably orally for LBSO and intravascularly for the ester, at a dose ranging from 1 to 10 mmol/kg, daily or at least two times a week, for at least 10 weeks.

Other patients in need of upregulation of nitrosative stress defenses besides those at risk for a cerebral stroke include, for example, those with neurodegenerative diseases such as Alzheimer's disease, Huntington's disease, amyotrophic lateral sclerosis, Parkinson's disease, and AIDS dementia; and those undergoing surgical procedures that might cause temporary reduction of blood flow to the brain.

The invention herein is illustrated by the following examples which are not intended to limit the invention.

EXAMPLE I

Inhibition of *E. coli* Gamma-Glutamylcysteine Synthetase by BSO Analogs

It has been known since the 1970's that methionine sulfoximine potently inhibits glutamine synthetase and gamma-glutamylcysteinyl synthetase (gamma-GCS) in mammalian systems. In 1978, O. W. Griffith and A. Meister reported that selective inhibition of either glutamine synthetase or gamma-GCS could be achieved using analogs of methionine sulfoximine. Thus, glutamine synthetase was inhibited by α-ethyl-DL-methionine-SR-sulfoximine, a compound which did not significantly inhibit gamma-GCS, and gamma-GCS was inhibited by DL-prothionine-SR-sulfoximine, a compound which did not significantly inhibit glutamine synthetase. Griffith, O. W., et al., J. Biol. Chem. 253, 2333–2338 (1978) and Griffith, O. W., et al., J. Biol. Chem. 254, 1205–1210 (1979). FIG. 5 in the second mentioned reference shows schematically the basis of this selectivity. As shown, the glutamate binding site of glutamine synthetase can accommodate α-alkyl substituents as large as ethyl, whereas the glutamate binding site of gamma-GCS cannot accommodate such substituents. Correspondingly, the binding site region occupied by S-alkyl substituents of homocysteine sulfoximine inhibitors is small in glutamine synthetase and much larger in gamma-GCS. Subsequent studies established that mammalian gamma-GCS is most effectively inhibited by L-buthionine-S-sulfoximine (BSO). Bacterial gamma-GCS, exemplified by the E. coli enzyme, catalyzes the same reaction as mammalian gamma-GCS, but the enzymes are essentially unrelated in terms of their protein structure and amino acid sequence. The possibility was therefore considered that homocysteine sulfoximine derivatives could be discovered that selectively inhibited E. coli gamma-GCS without inhibiting the mammalian enzyme.

E. coli gamma-GCS was isolated from bacterial cells engineered to overexpress the enzyme; the isolation procedure was similar to that used previously to isolate mammalian gamma-GCS. The enzyme obtained was pure by polyacrylamide gel electrophoresis in the presence of denaturants (SDS-PAGE) and had a specific activity of ~1,100 units/mg. The enzyme was assayed in reaction mixtures (final volume=1.0 ml) containing: 150 mM Tris*HCl, pH 8.2, 100 mM KCl, 25 mM MgCl$_2$, 7.5 mM ATP, 7.5 mM phosphoenolpyruvate, 0.3 mM EDTA, 10 mM L-glutamate, 10 mM L-α-aminobutyrate (an L-cysteine analog), 0.3 mM NADH, 5 IU pyruvate kinase, and 5 IU lactate dehydrogenase. Reaction was initiated by adding gamma-GCS; in control studies, L-α-aminobutyrate was omitted from the reaction mixture. In this assay, pyruvate kinase (PK) and lactate dehydrogenase (LDH) are added in excess to detect formation of ADP, one of the products of the gamma-GCS reaction. The relevant enzyme reactions are shown as equations 1–3 below. Oxidation of NADH to NAD$^+$ is followed and quantitated spectrophotometrically at 340 nm (1 μmol oxidation gives ΔOD=−6.2) and is directly proportional to product formation by gamma-GCS.

Reaction 1:

Glutamate + L-α-aminobutyrate + ATP 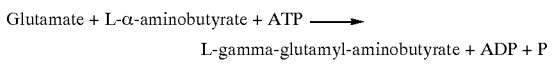

L-gamma-glutamyl-aminobutyrate + ADP + P

Reaction 2:

ADP + phosphoenolpyruvate  ATP + pyruvate

Reaction 3:

Pyruvate + NADH  Lactate + NAD$^+$

Inhibition by homocysteine sulfoximines was carried out by preincubating the E. coli gamma-GCS with potential inhibitors in the presence of ATP and then removing aliquots of that mixture at specific times and assaying for residual activity using the assay procedure described above. The preincubation reaction mixtures contained (final volume= 400 μl) the following: 210 mM Tris*HCl, pH 8.2, 142 mM KCl, 36 mM MgCl$_2$, 10 mM ATP, 0.4 mM EDTA, various amounts of sulfoximine, and gamma-GCS. At intervals, 50 μl aliquots were removed and added to 1.0 ml assay reaction mixtures to determine residual activity spectrophotometrically. Results of a study indicate that E. coli gamma-GCS loses about 27% of its activity over 30 minutes in the absence of added inhibitors; this loss of activity represents an inherent instability in the enzyme when incubated under these reaction conditions in this particular experiment. Inclusion of 100 μM L-buthionine-S-sulfoximine (L-BSO) results in 89% inactivation in 10 min and virtually complete inactivation in 30 min. A similar level of inactivation was achieved with 2 mM with α-ethyl-DL-buthionine-SR-sulfoximine (DL-SR-α-ethyl-BSO), synthesized by the method described in Griffith, O. W., Methods in Enzymology, 143, 286–291 (1987) for synthesizing DL-α-ethylmethionine-SR-sulfoximine except 45.1 g (0.5 mole, approximately 53.6 ml) of 1-butanethiol was used in place of methanethiol. (Analytical date on the synthesized compound is given above; the synthesized compound was greater than 95% pure by high performance liquid chromatography (HPLC) using the HPLC procedure with solvent system described in Griffith, O. W., et al., Methods in Enzymology, 143, 166–172, (1987)). This preparation contains 4 isomers of α-ethyl-BSO, but only the L-S isomer is active as an enzyme inhibitor. The concentration of α-ethyl-L-buthionine-S-sulfoximine is ~¼ of the total concentration or ~500 μM. Therefore, the experiment shows that on an active isomer basis α-ethyl-BSO is about 20% as effective an inhibitor of E. coli gamma-glutamylcysteine synthetase as is L-S-BSO. Note that α-ethyl-BSO will not inhibit glutamine synthetase because its S-alkyl substituent is too large to bind to that enzyme (see said FIG. 5 mentioned above). In separate studies, α-ethyl-DL-buthionine-SR-sulfoximine was compared to L-buthionine-S-sulfoximine as an inhibitor of mammalian gamma-GCS. Using highly purified rat kidney gamma-GCS and a protocol similar to that described here for the E. coli enzyme, it was found that α-ethyl-DL-buthionine-SR-sulfoximine was 0.025% as effective as L-buthionine-S-sulfoximine as an inhibitor of the mammalian enzyme. Expressed on the basis of the active isomer, α-ethyl-L-buthionine-S-sulfoximine, α-ethyl-BSO has about 0.1% the inhibitory activity of L-buthionine-S-sulfoximine with mammalian enzyme.

EXAMPLE II

Proof That Nitrosating Agent Causes Reduction in Bacterial Growth and That Pretreatment With Nitrosating Agent Induces Resistance to Later Treatment With Nitrosating Agent In a first experiment, six runs were carried out. In three of the runs, wild type E. coli were incubated in bacterial growth medium. In the other three runs, E. coli lacking a gene essential for glutathione production (in particular, lacking a gene expressing gamma-glutamylcysteine synthetase, hereinafter glutathione deficient E. coli) were incubated in the bacterial growth medium. In one run, for each of the wild type E. coli and the glutathione deficient E. coli, no nitrosating agent was employed. In one run, for each of the wild type E. coli and the glutathione deficient E. coli, 0.5 mM S-nitrosocysteine (a nitrosating agent) was added after two hours. In one run, for each of the wild type E. coli and the glutathione deficient E. coli, 0.2 mM S-nitrosocysteine was added initially and 0.5 mM S-nitrosocysteine was added at the two hour mark. In each run, starting at the two hour mark and every 15 or 30 minutes thereafter, bacterial cell density (i.e., growth) was measured. The results are shown in FIG. 1 where cell density is plotted versus time (after two hours) and where O.D. 600 nm is a measure of bacterial cell growth, "wt" stands for wild type E. coli, "Δgsh" stands for glutathione deficient Reaction E. coli, a minus sign under "pre" means no pretreatment with 0.2 mM S-nitrosocysteine, a plus sign under "pre" means pretreatment with 0.2 mM S-nitrosocysteine, a minus sign under "post" means no post-treatment with 0.5 mM S-nitrosocysteine, a plus sign under "post" means post-treatment with 0.5 mM S-nitrosocysteine. Thus the circle data points are for wild type *E. coli* with no S-nitrosocysteine treatment; the X data points are for glutathione deficient *E. coli* with no S-nitrosocysteine treatment; the diamond data points are for wild type *E. coli* with treatment with both 0.2 mM S-nitrosocysteine and 0.5 mM S-nitrosocysteine. The triangle data points are for glutathione deficient *E. coli* with treatment with both 0.2 mM S-nitrosocysteine and 0.5 mM S-nitrosocysteine; the square data points are for wild type *E. coli* with no 0.2 mM S-nitrosocysteine treatment but with 0.5 mM S-nitrosocysteine treatment; and the plus sign data points are for glutathione deficient *E. coli* with no 0.2 mM S-nitrosocysteine treatment but with 0.5 mM S-nitrosocysteine treatment.

Figure 2:
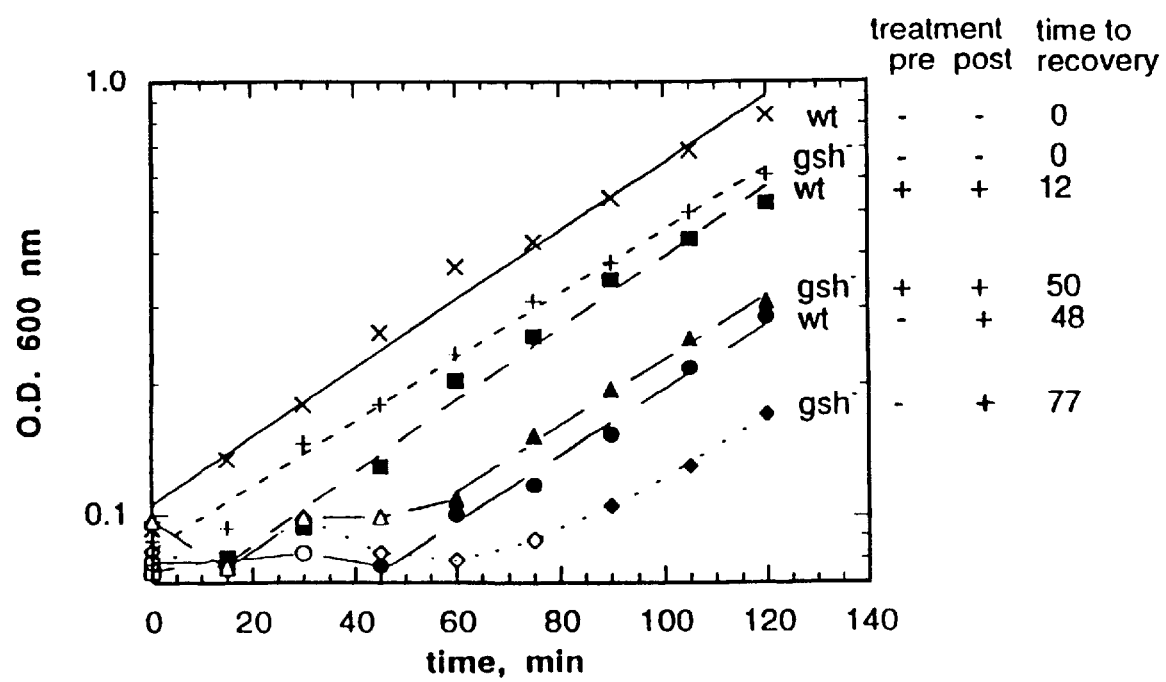
FIG. 2 is a graph where cell density is plotted on a log axis versus time where O.D. 600 nm is a measure of bacterial growth; it graphically depicts results of Example II.

In a second experiment, six runs were carried out the same as in the first experiment. In this case, the results are shown in FIG. 2 where bacterial growth (measured as optical density (O.D.) 600 nm) is plotted on a log axis versus time (after two hours) and where "wt" and the plus and minus sign mean the same as in FIG. 1 and "gsh$^-$" means glutathione deficient *E. coli*. In FIG. 2, the X data points are for wild type *E. coli* with no S-nitrosocysteine treatment; the plus sign data points are for glutathione deficient *E. coli* with no S-nitrosocysteine treatment; the square data points are for wild type *E. coli* with treatment with both 0.2 mM S-nitrosocysteine and with 0.5 mM S-nitrosocysteine; the triangle data points are for glutathione deficient *E. coli* with treatment with both 0.2 mM S-nitrosocysteine and with 0.5 mM S-nitrosocysteine; the circle data points are for wild type *E. coli* with no treatment with 0.2 mM S-nitrosocysteine but with treatment with 0.5 mM S-nitrosocysteine; and the diamond data points are for glutathione deficient *E. coli* with no treatment with 0.2 mM S-nitrosocysteine but with treatment with 0.5 mM S-nitrosocysteine. In FIG. 2, the open symbols (i.e., symbols which are not filled in, i.e., not solid) represent no growth. In FIG. 2, the use of a semilog scale provides linear rate of growth of curves, in the absence of treatment, i.e., depicts "log phase growth" as a straight line.

The results demonstrate that nitrosating agent reduces rate of bacterial growth, that there are two ways of inhibiting bacterial growth (delaying growth and causing failure to achieve maximal growth), that glutathione itself protects against nitrosative stress but is also involved in other protections against nitrosative stress (i.e., glutathione helps the organism induce resistance to nitrosative stress).

The same results were obtained when the experiment was carried out under anaerobic conditions. This indicates that nitrosative stress is involved and not oxidative stress. Moreover, the levels of reduced thiol were elevated in the experiments indicating that the cells continue to maintain reduced intracellular environment inconsistent with oxidative stress. In other words, in all the cells, thiol levels went up even through glutathione level was down, indicating oxidative stress is not involved.

EXAMPLE III

A patient with *E. coli* caused gastroenteritis with bloody diarrhea is administered α-ethyl-L-buthionine-S-sulfoximine (hereinafter α-ethyl BSO) orally at a dose of 10 mmol/kg body weight four times a day. Bloody diarrhea resolved over four days. Similar results obtained using the same dose of α-ethyl-L-buthionine-S-sulfoximine given intravenously at the same dose.

EXAMPLE IV

A patient with *E. coli* caused gastroenteritis and bloody diarrhea is administered α-ethyl BSO orally at a dose of 10 mmol/kg body weight four times a day. In addition, the patient is given chloramphenicol orally at a dose of 12.5 mg/kg four times a day. Bloody diarrhea resolved in 36 hours. Chloramphenicol normally has effect in three days.

EXAMPLE V

A patient infected with *Actinomycetes israelii* has a low-grade fever, non-productive cough, and occasional hemoptysis. The patient is given serinyl-S-nitrosocysteinyl-gluatamine at a dose of 1 mg/kg body weight four times per day i.v. The patient's symptoms resolve over three weeks.

EXAMPLE VI

A patient reports having a cough, hemoptysis and weight loss extending over several months. A culture of sputum shows drug-resistant *Mycobacterium tuberculosis*. The patient is admitted to the hospital and is given NO-substituted isoniazid at a dose of 300 mg once a day p.o. for one week and rifampin at a dose of 600 mg per day p.o. for one week. After one week, the patient has become tolerant of the hypotensive effect of NO-substituted isoniazid and is discharged from the hospital with instructions to continue the same medications at the same dose for nine months. During that period, cough and hemoptysis resolve, and the patient returns to his normal weight.

Similar results are obtained using NO-substituted rifampin and isoniazid at doses of 600 mg and 300 mg per day, respectively.

Another patient with drug resistant tuberculosis is placed on conventional therapy of isoniazid (300 mg/day), rifampin (600 mg/day) and ethambutol (15 mg/kg/day). Over a period of several weeks, the patient develops a loss of color vision and gastrointestinal intolerance attributable to ethambutol. NO-substituted isoniazid (300 mg/day p.o.) and NO-substituted rifampin (600 mg/day p.o.) were given as an alternative therapy, and the patient recovered.

EXAMPLE VII

An immunocompromised patient recovering from bone marrow transplantation develops a lump in his cheek at a place previously scratched by a garden implement. A culture obtained from the lump is positive for Streptomycetes. The patient is given DL-α-amino-δ-butylthio valeric acid-SR-sulfoximine at a dose of 4 mmol/kg body weight three times a day p.o. The patient is also given trimethoprim (160 mg twice a day) and sulfamethoxazole (800 mg twice a day) for one month. The lesion in patient's cheek resolves completely.

EXAMPLE VIII

A patient with septicemia has a blood pressure of 80/55 mmHg and a positive blood culture for *E. coli*. The patient is given a vector containing an antisense construct to the OxyR promotor at a dose of 25 μg/kg twice a day in 50 ml saline i.v. The patient is also given chloramphenicol at a dose of 15 mg/kg four times a day i.v. Blood pressure returned to normal in 48 hours and a repeat blood culture is negative.

EXAMPLE IX

A 43 year old woman with fever, mild hypotension, and moderate hematuria has blood and urine cultures that are positive for *E. coli*. She is given a diagnosis of *E. coli* septicemia and urinary tract infection. She is treated with α-ethyl BSO at a dose of 4 mmol/kg four times a day p.o. and S-nitroso-gamma-methyl-L-homocysteine at a dose of 50 μg/kg body weight i.v. She is also given gentamicin at a loading dose of 2 mg/kg body weight followed by 1 mg/kg body weight every 12 hours i.v. All of her symptoms resolve and blood and urine cultures are negative for *E. coli* after two weeks.

EXAMPLE X

A patient with septicemia due to Salmonella exhibits hypotension, dyspepsia and diarrhea. He is given 200 mg/kg sodium nitrate i.v. twice a day and is also give ethacrynic acid at a dose of 50 mg four times a day p.o. All of the patient's symptoms resolve in two days.

EXAMPLE XI

A 25 year old woman with a history of multiple sexual partners and recurrent urinary tract infections presents with cervicitis and vaginitis of four days duration. The patient complains of pain and vaginal discharge. A culture of the cervix is positive for *Chlamydia trachomatous* and no other pathogen. The patient is given 500 mg of tetracycline four times a day p.o. The infection proves difficult to eradicate. The patient is then given the nitrate ester of tetracycline at a dose of 500 mg four times a day p.o. With this latter regimen, the patient's symptoms resolve and her cervical culture becomes negative in two weeks.

A similar patient is successfully treated using the nitrate ester of chloramphenicol. In this case, the patient is given α-ethyl BSO at a dose of 4 mmol/kg four times a day p.o. and the nitrate ester of chloramphenicol at a dose of 12.5 mg/kg body weight four times a day p.o. The infection resolves in 10 days.

EXAMPLE XII

A 27 year old homosexual white male complains of chronic diarrhea, weight loss, and flatulence of approximately three weeks duration. A stool sample is found to be positive for *Giardia lamblia*. The patient is given L-buthionine-S-sulfoximine (4 mmol/kg four times a day p.o.) and metronidazole (Flagyl; 500 mg twice a day p.o. for five days). The symptoms resolve and the stool culture becomes negative for Giardia after five days.

Three months later the same patient presents with a similar history of chronic diarrhea, weight loss and flatulence. The patient is treated similarly except that the nitrate ester of metronidazole is used in place of metronidazole itself; the dose remains 500 mg twice a day p.o. The patient's symptoms resolve and stool culture becomes negative one day earlier than in the previous episode.

EXAMPLE XIII

A 50 year old male presents with rash and fever. He reports that he has recently returned from a camping trip to the mountains. A tentative diagnosis of Rocky Mountain Spotted Fever (rickettsia) is made, and the patient is given α-ethyl BSO (4 mmol/kg body weight four times a day p.o.) and chloramphenicol (12.5 mg four times a day p.o.). The patient becomes well in 10 days.

EXAMPLE XIV

A 30 year old man from Kentucky presents complaining of weight loss, fever, night sweats and cough of two months duration. Chest X-ray shows bilateral infiltrates, and the patient has a positive serum titer of 1:32 for *Histoplasma capsulatum*. The patient's sputum also cultures positive for *Histoplasma capsulatum*. The patient is given a diagnosis of histoplasmosis and is treated with amphotericin B at a dose of 1 mg/day i.v. After one week, the patient is found to have an elevated blood urea nitrogen level and other evidence of renal failure. The amphotericin B dose is reduced to 0.5 mg/day, but there is no resolution of disease. The patient is then given NO-substituted amphotericin B at a dose of 0.5 mg/day for a total dose of 1 gm. After 10 weeks, the patient's symptoms fully resolve.

EXAMPLE XV

A 23 year old white male presents with a history of fever and productive cough. A chest X-ray shows bilateral infiltration. The patient's sputum is negative. The patient is given a presumed diagnosis of mycoplasma pneumonia and is treated with erythromycin (500 mg three times a day p.o.). Due to gastrointestinal distress, the dose is reduced to 250 mg three times a day, but the patient's symptoms linger. The patient is then given 250 mg of NO-substituted erythromycin, and all signs and symptoms resolve in 10 days.

EXAMPLE XVI

A patient with *E. coli* septicemia confirmed by positive blood culture and with a blood pressure of 80/50 mmHg is found to be resistant to conventional antibiotic therapy. The patient is given α-ethyl BSO (4 mmol/kg four times a day p.o.) and is placed in a hyperbaric chamber pressurized to 3 atmospheres of 100% oxygen once a day for four days. Conventional antibiotic therapy with ampicillin (1 gm i.v. six times a day) and gentamicin (1 mg/kg body weight i.v. twice a day) is continued. The patient's symptoms resolve within four days with blood pressure returning to normal and blood culture being negative for *E. coli*.

EXAMPLE XVII

A patient with lymphadenopathy and a diagnosis of Stage IV Hodgkin's Disease is failing conventional therapy and is treated with BCNU (carmustine; 300 mg/m$^2$ on day one) and NO-substituted melphalan (140 mg/m$^2$ on day six). The therapy is repeated in three weeks. The patient experiences a partial remission of his disease.

EXAMPLE XVIII

A 67 year old white male with a 80 pack-year history of smoking presents with hemoptosis and weight loss. Chest X-ray shows a hilar mass and the patient's sputum is positive for small cell lung cancer. The patient is given a combination therapy of cyclophosphamide (750 mg/m$^2$) plus NO-substituted doxirubicin (40 mg/m$^2$) and vincristine (2 mg) (all administered i.v.). The therapeutic regimen is repeated once at three weeks. Repeat of the chest X-ray shows a 33% reduction in the hilar mass.

EXAMPLE XIX

A 55 year old white male smoker presents with chest pain. His coronary angiogram shows 99% left anterior descending coronary artery stenosis. The patient is treated with 80 mg verapamil three times a day p.o. and with L-buthionine-S-sulfoximine, i.e., BSO (4 mmol/kg i.v. four times a day). A stent constructed of a NO-releasing polymer is placed in the constricted artery. The patient rapidly becomes pain free and a repeat angiogram at six months shows no restenosis.

A patient similar to the one described above is treated with a BSO-releasing polymer stent and is given S-nitrosocysteine (100 nmol/kg body weight over one min.) by intracoronary infusion. The patient reports no chest pain and a follow-up angiogram shows no restenosis.

A third patient also having 99% occlusion of his left anterior descending coronary artery is given BSO (4 mmol/kg four times a day by direct intracoronary infusion) and a Palmaz-Schatz stent implanted with radioactive $^{32}$P is placed in his left anterior descending artery. BSO therapy is continued for one week. The therapy is successful; the patient experiences no further chest pain and repeat of his angiogram shows no restenosis. A similar patient is treated with the Palmaz-Schatz $^{32}$P-implanted stent but is given S-nitrosocysteine (100 nmol/kg body weight over one min. six times a day for one week by direct intracoronary infusion). The therapy successfully prevents restenosis as confirmed by repeat of the patient's angiogram. A similar patient with somewhat more extensive disease was treated similarly with Palmaz-Schatz $^{32}$P-implanted stent and S-nitrosocysteine, but this patient is also given ethacrynic acid (50–200 mg, twice a day, p.o.) to effect thiol depletion. The patient's symptoms improve.

EXAMPLE XX

A 65 year old white male presents with a history of urinary hesitancy and multiple awakenings during the night. He is given a diagnosis of benign prostatic hypertrophy. Under stereotactic guidance, the patient's enlarged prostate gland is implanted with several porus polymer pellets designed to slowly release buthionine-S-sulfoximine (1 $\mu$mol/hr) and S-nitrosocysteine (1 $\mu$mol/hr). The patient's symptoms improve over a period of three weeks. He then has nearly normal urine flow and usually wakes no more than once per night.

A similar patient with benign prostatic hypertrophy and very marked enlargement of his prostate is treated with NO-substituted finasteride (NO-substituted Proscar; 5 mg/day). NO-substitution is accomplished by replacement of the tert-butyl amine moiety of finasteride with S-nitroso-$\beta$-thio-tert-butyl amine. The patient's symptoms improve.

EXAMPLE XXI

A patient with septicemia (bp=80/50 mmHg and blood culture positive for *E. coli*) is treated with S-nitrosocysteine (100 nmol/kg body weight i.v.) and shows a partial remission in his disease accompanied by mild hypotension. While continuing S-nitrosocysteine therapy, the patient is also given desferoximine (1 gm followed by 0.5 gm every 4 hr for two days) with relief of hypotension and complete resolution of septicemia.

EXAMPLE XXII

A patient with Salmonella gastroenteritis presents with intestinal pain and bloody diarrhea. The patient receives chloramphenicol orally at a dose of 12.5 mg/kg, four times a day together with IV administration of 100 $\mu$g/kg of an antisense construct against the metL gene. The diarrhea subsides in 24 hours.

EXAMPLE XXIII

A patient with cough and hemoptysis for two weeks has a sputum culture showing microbacterium tuberculosis. The patient is given NO$_2$-substituted isoniazid at a dose of 300 mg once a day p.o. for one week and rifampin at a dose of 600 mg/day p.o. for one week and melphalan at a dose of 6 mg/day p.o. for one week. The patient's symptoms resolve and he is sent home on the same drug at the same dose for nine months except that melphalan is omitted in weeks 3, 4, 5 and 6.

EXAMPLE XXIV

A 36 year old black female presents with *E. coli* sepsis and a blood pressure of 90 mmHg. The patient is given a vector containing an antisense construct to the oxyR promoter I.V. at a dose of 25 mg/kg twice a day in 15 ml of saline. In addition, she is also treated with $\alpha$-ethyl BSO, orally, at a dose of 4 mmol/kg four times a day. Symptoms resolve and the blood pressure is restored within 24 hours. The therapy is continued for two weeks.

EXAMPLE XXV

A patient with schistomasis presents with symptoms of pruritic dermatitis, cough, diarrhea, fever and tender hepatosplenomegaly. Diagnosis is made by eggs of *S. japonicum* found in the stool. The patient is given anti *S. japonicum* antibody cross-linked by ester linkage to L-buthionine-S-sulfoximine I.V. at a dose of 500 mg for one day together with praziquantel (60 mg/kg p.o. in two divided doses over one day). The symptoms resolved and do not recur.

EXAMPLE XXVI

A 70 year old black male with a 20 pack/year history of smoking presents with cough. His chest X-ray showed a small peripheral mass that was biopsy-positive for small-cell lung cancer. The patient receives cyclophosphamide (750 mg/m$^2$ and NO-substituted doxirubicin (administered IV)). The patient also receives L-buthionine-S-sulfoximine, i.e., BSO (4 mmol/kg IV four times/day). A repeat chest X-ray in two months shows decrease in size of the mass.

EXAMPLE XXVII

A 45 year old black male with blue eyes and gray hair presents with chest pain. His coronary angiogram shows an 80% occlusion of his left anterior descending coronary artery before the first diagonal. The patient undergoes balloon angioplasty and placement of a Palmaz-Schatz stent, which is P$^{32}$-implanted and coated with a cyclodextran polymer to which BSO is attached by an ester linkage. The patient's symptoms resolve and clinical restenosis does not occur.

A patient similar to the one described above undergoes balloon angioplasty and placement of a Palmaz-Schatz stent which is coated with cyclodextran polymer to which ethyl maleate is attached by an ester linkage. The patient's symptoms resolve and clinical restenosis does not occur.

EXAMPLE XXVIII

A 62 year old white male with restenosis four months post angioplasty has a Palmaz-Schatz stent placed. A construct containing antisense to the promoter of human transaldolase is locally administered into the vessel wall by a drug delivery balloon at a dose of 100 $\mu$g at the time of stent placement. Symptoms resolve and clinical restenosis does not occur.

EXAMPLE XXIX

A 60 year old black male smoker presents with chest pain. His coronary angiogram shows 75% occlusion of the left circumflex coronary artery. He has a Palmaz-Schatz stent placed which is coated with a porous polymer containing 10% NO-substituted L-butathione-S-sulfoximine by weight of the polymer. Drug delivery from the stent occurs over two days. Symptoms resolve and clinical restenosis does not occur.

EXAMPLE XXX

A 65 year old white male with three-vessel disease status post cabbage presents with chest pain. His angiogram shows that his saphenous vein graft to the right coronary artery has closed. A Palmaz-Schatz stent coated with an ONO-substituted polymer to which melphalan has been chemically attached in an amount of 10% by weight of the polymer is placed. The patient's symptoms resolve and clinical restenosis does not occur.

EXAMPLE XXXI

A 60 year old white male with benign prostatic hypertrophy is treated with Finisteride (Proscar: 5 mg/day) and oral buthionine-S-sulfoximine at a dose of 10 mmol/kg four time/day. His symptoms of hesitancy improve significantly over two months.

EXAMPLE XXXII

An immunocompromised white male who is status-post recent chemotherapy develops oral thrush. He is given 5 cc 50 mM acidified nitrite, swish and spit, four times/day and his soreness and pain resolve over two days.

EXAMPLE XXXIII

A 70 year old white male with leukemia develops oral thrush and is given 2 cc of 50 mM S-nitrosoglutathione, swish and spit, three times/day. The pain starts to resolve in one day and is much improved in three days.

EXAMPLE XXXIV

A 25 year old runner develops athlete's foot. He applies Micatin (miconazole) cream, but symptoms are slow to resolve over three weeks. He substitutes a cream containing the same ingredients, with the exception that S-nitroso-N-acetyl cysteine has been added so as to be present at a concentration of 50 mM. His symptoms improve over seven days.

EXAMPLE XXXV

A 30 year old white male marathon runner develops athlete's foot. He treats himself with a topical mixture of inorganic nitrite, acetic acid and thiol in a cream base. His symptoms resolve over three weeks.

EXAMPLE XXXVI

A 30 year old white female with *E. coli* sepsis presents feeling nauseated and gravely ill. However, her blood pressure is stable. She receives a standard regimen of IV antibiotics, including ampicillin and gentamicin as well as the siderophore ferrioxamine B at a dose of 10 mg/kg. The patient's symptoms resolve and she does not develop the clinical syndrome of hypotension and organ failure. However, a similar patient who did not receive the metal chelator goes on to develop severe hypotension requiring prolonged stay in the Intensive Care Unit.

EXAMPLE XXXVII

A 60 year old patient with diabetes develops a skin ulcer on the lower aspect of his left leg. Cultures grow mixed flora and gram-negative rods. A topical cream is applied that contains S-nitrosoglutathione, oxidized glutathione and the glutathione S-conjugate dinitrophenacyl glutathione. The culture of the ulcer becomes sterile over three days and starts to improve.

EXAMPLE XXXIX

A 40 year old woman with *E. coli* sepsis presents with a blood pressure of 80/50 mm Hg. Broad spectrum antibiotics are initiated including ampicillin and gentamicin. However, the patient's course does not improve within the next 24 hours, at which time her blood pressure is 85 systolic. The patient then receives an intravenous dose of nitrosated chloramphenicol, 12.5 mg four times/day IV together with methylene blue IV at a dose of 5 mg/kg as well as fluid support. The blood pressure is gradually restored over 24 hours and the patient's symptoms improve. In contrast, the same patient who is not given methylene blue developes worsening hypotension on administration of the nitrosant.

EXAMPLE XL

A 20 year old white homosexually active male developed a recurrent herpes labialis (cold sore) on his lips and face. Therapy with Denavir (pencicyclovir cream) that contains buthionine sulfoximine is applied topically every two hours while awake. The mean duration of the lesion is half the time shorter than that of a similar subject treating himself with Denivir that does not contain BSO.

EXAMPLE XLI

A 70 year old white male with bilateral 90% stenoses of his corotid arteries has three transient ischemic attacks over 24 hours. He is not a surgical candidate. He is taken to the hyperbaric chamber and given 100% oxygen with 80 ppm (part/million) NO in 3 atmospheres of absolute pressure. Treatment is given three times/day for ten days. The patient subsequently has a small stroke but recovers well and maintains function. A similar patient who does not receive prophylactic therapy against nitrosative stress has a large stroke and loses use of the left side of his body.

EXAMPLE XLII

A 40 year old immunocompromised white male with HIV and a low CD4 count develops oral thrush. He is given 5 cc of a solution of 10 mM nitrate. His thrush resolves.

EXAMPLE XLIII

A 50 year old male with restenosis six months post angioplasty has a Palmaz-Schatz stent placed. The stent is coated with a porous polymer containing 10% of the siderophore ferrioxamine B and 0.1% each of interleukin-1 and interferon-gamma. The latter agents induce the local expression of the inducible isoform of nitric oxide synthase. The patient makes an uneventful recovery from surgery and restenosis does not occur.

EXAMPLE XLIV

A 56 year old male of Scandinavian descent and a history of surgery five years previously to remove malignant melanotic nevi from his upper back and chest is found to have blood in his stool on routine physical examination. Follow-up colonoscopy shows metastatic malignant melanoma partially obstructing the proximal small bowel. The patient is administered L-buthionine-S-sulfoximine (2 mmol/kg) p.o.

every 4 hours for one week and is given 10 mg/kg of hydroxyurea p.o. 1 hour after every third dose of L-buthionine-S-sulfoximine. After one week, the metastatic tumor shows increased areas of focal necrosis, is reduced in size by 30% and is removed surgically. The patient shown no further evidence of metastases during a six month follow-up.

EXAMPLE XLV

A 50 year old male with restenosis five months post angioplasty has a Palmaz-Schatz stent placed. The stent is coated with a porous polymer containing 10% by weight of NO-substituted verapamil which is released from the polymer at the rate of 1 μg/hr. Symptoms resolve and clinical restenosis does not occur.

EXAMPLE XLVI

A 37 year old male presents with high fever, moderate lymphadenopathy and reports that he has lost 40 pounds in the last month, two months after returning from a safari in sub-Saharan Africa. On questioning, the patient reports having developed during the safari an ulcer on his forearm two days following a bite by a fly. Microscopic examination of a blood smear shows the presence of trypanosomes. The patient is hospitalized and given L-buthionine-S-sulfoximine at a dose of 3 mmol/kg p.o. every 4 hours for one week. In addition, the patient receives S-nitrosoglutathione iv at a dose of 10 mg/kg every 8 hours for one week. After one week, a blood smear is free of trypanosomes, and the patient remains symptom free and returns to his original weight over the following two months.

REFERENCE EXAMPLE

A recent CNN report described an explosion of a tanker containing the toxic nitrosant gases $NO_2/N_2O_4$. The cloud of gas 12 remained in the area for several days, was blown away and then blown back several days later. Subjects in the area developed respiratory infections and cognitive and central nervous system deficits. However, workers in the $N_2O_4$ plant who were exposed chronically to low doses of $N_2O_4$ on a regular basis were found to be protected from the brain syndrome.

Variations of the invention will be obvious to those skilled in the art. Therefore the invention is defined by the claims.

What is claimed is:

1. α-alkyl-S-alkyl-homocysteine sulfoximines wherein the α-alkyl contains 2 to 8 carbon atoms and the S-alkyl contains 1 to 10 carbon atoms except for α-ethyl-methionine sulfoximine.

2. A sulfoximine as claimed in claim 1 which is the L,S-diastereomer.

3. A sulfoximine as claimed in claim 2 which is α-ethyl-L-buthionine-S-sulfoximine.

4. A sulfoximine as claimed in claim 1 which is selected from the group consisting of α-ethyl-buthionine sulfoximine, α-propyl-buthionine sulfoximine, α-isopropyl-buthionine sulfoximine, α-butyl-buthionine sulfoximine, and α-tert butyl-buthionine sulfoximine.

5. A sulfoximine as claimed in claim 4 which is the L,S-diastereomer.

6. A sulfoximine which is the ethyl ester or the isopropyl ester and/or is the N-α-acetylated derivative of a sulfoximine as claimed in claim 4.

7. A sulfoximine as claimed in claim 6 which is the L,S-diastereomer.

8. A sulfoximine as claimed in claim 1 where the S-alkyl contains 2 to 10 carbon atoms.

9. A sulfoximime as claimed in claim 8 which is the L,S-diastereomer.

10. A sulfoximine as claimed in claim 1 wherein the S-alkyl contains 3 to 10 carbon atoms.

11. A sulfoximine as claimed in claim 10 which is the L,S-diastereomer.

12. A sulfoximine which is the ethyl ester or the isopropyl ester and/or is the N-α-acetylated derivative of a sulfoximine as claimed in claim 1.

13. A sulfoximine as claimed in claim 12 which is the L,S-diastereomer.

14. A sulfoximine as claimed in claim 1 wherein the homocysteine is replaced by thionorvaline.

15. A sulfoximine as claimed in claim 14 which is selected from the group consisting of α-ethyl-S-butyl-δ-thionorvaline sulfoximine and α-propyl-S-butyl-δ-thionorvaline sulfoximine.

* * * * *

UNITED STATES PATENT AND TRADEMARK OFFICE
CERTIFICATE OF CORRECTION

PATENT NO. : 6,180,824 B1
DATED : January 30, 2001
INVENTOR(S) : Jonathan S. Stamler and Owen W. Griffith It is certified that error appears in the above-identified patent and that said Letters Patent is hereby corrected as shown below:

<u>Title page,</u>
"OTHER PUBLICATIONS", add the following:
-- Bahr, N., et al., J. Am. Chem. Soc. 118, 3550-3555 (1996)
Griffith, O. W., et al., J. Biol. Chem. 253, 2333-2338 (1978)
Apontoweil, P., et al., Biochimica et Biophysica Acta 399, 10-22 (1975)
Bogle, R. G., et al., Br. J. Pharmacol 105, 768-770 (1992) --.

Signed and Sealed this

Twenty-third Day of October, 2001

Attest:

*Nicholas P. Godici*

NICHOLAS P. GODICI
*Attesting Officer*   *Acting Director of the United States Patent and Trademark Office*